(12) United States Patent
Liang et al.

(10) Patent No.: US 9,845,467 B2
(45) Date of Patent: Dec. 19, 2017

(54) COMPOUNDS AND METHODS FOR MODULATING TARGET NUCLEAR AND SUB-NUCLEAR NUCLEIC ACID MOLECULES IN CELLS AND ANIMALS

(71) Applicants: Ionis Pharmaceuticals, Inc., Carlsbad, CA (US); Cold Spring Harbor Laobratory, Cold Spring Harbor, NY (US)

(72) Inventors: Xue-hai Liang, Del Mar, CA (US); Stanley T. Crooke, Carlsbad, CA (US); C. Frank Bennett, Carlsbad, CA (US); David L. Spector, Cold Spring Harbor, NY (US)

(73) Assignees: Ionis Pharmaceuticals, Inc., Carlsbad, CA (US); Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 15/061,843

(22) Filed: Mar. 4, 2016

(65) Prior Publication Data

US 2016/0194637 A1    Jul. 7, 2016

Related U.S. Application Data

(63) Continuation of application No. 13/811,248, filed as application No. PCT/US2011/044567 on Jul. 19, 2011, now abandoned.

(60) Provisional application No. 61/365,765, filed on Jul. 19, 2010.

(51) Int. Cl.
*A61K 48/00* (2006.01)
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/341* (2013.01); *C12N 2310/351* (2013.01); *C12N 2310/3521* (2013.01); *C12N 2310/3525* (2013.01); *C12N 2310/3533* (2013.01); *C12N 2320/30* (2013.01)

(58) Field of Classification Search
CPC ..................................................... A61K 48/00
See application file for complete search history.

(56) References Cited

U.S. PATENT DOCUMENTS

2006/0079471 A1* 4/2006 Michaeli ................ C07H 21/02
                                                                    514/44 A
2008/0242629 A1* 10/2008 Crooke ................. C12N 15/113
                                                                    514/44 A

OTHER PUBLICATIONS

Mowry et al. (Science Dec. 1987, Voi. 238: 1682-1687).*

* cited by examiner

*Primary Examiner* — Kimberly Chong
(74) *Attorney, Agent, or Firm* — McNeil Baur PLLC

(57) ABSTRACT

The present invention provides compounds and methods for modulating target nucleic acids found in organelles or sub-organelles of cells. The invention includes, but is not limited to compounds and methods that modulate target nucleic acids in a sub-nuclear organelle, such as the nucleolus and/or a cajal body. In certain embodiments, the cell is in an animal.

15 Claims, 13 Drawing Sheets

Fig-1

5' RmRmRmRmddddddddRmRmRmRm 3'

5'- cuucauuuau augggüuau uuugcu UGCA AUGAUGUCGU AAUUGCGU UUACUCUGUU

CUCAGGGACA GUGCCUGCU GUCAGUAAGC UGGUACAGAA GGUUGACGAA AAUUCUUACU GAGCAA gaaauaaccuuguu guaauuacua -3'

Fig 27
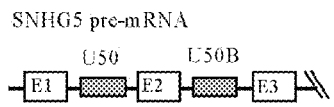
SNHG5 pre-mRNA
Fig 28
```
            10        20        30        40        50
U50   TA-TCTGTGATGAT-CTTATCCCGAACCTGA--ACTTCTGTTGAAAAAAAAAAACTTTTA
      ::  ::  :::::: : :::::::::: ::::  ::  :   ::::  ::::: ::  :  :
U50B  TAATCAATGATGAAACCTATCCCGAAGCTGATAAC---C---TGAAGAAAAATAAGT---A
            10        20        30           40        50
            60        70
U50   CGGAT-CTGGCTTCTGAGAT
      :::::  : ::::::::::::
U50B  CGGATTC-GGCTTCTGAGAT
            60        70
```
Fig 29
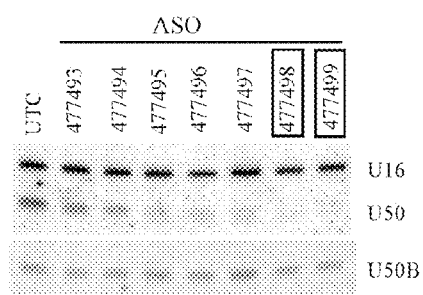
Fig 32
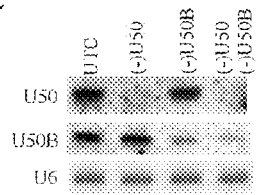
Fig 30
```
ASO477499  3' AAUGCctagaccgaaGACUC 5'
              ||||||||||||||||||||
U50 RNA    5'-UUACGGAUCUGGCUUCUGAG₇₃-3'
              ||||||  ||||||||||
U50B RNA   5'-GUACGGAUUCGGCUUCUGAG₆₉-3'
              ||||||||||||||||||||
ASO485259  3' GAUGCctaagccgaaGACUC 5'
```
Fig 33
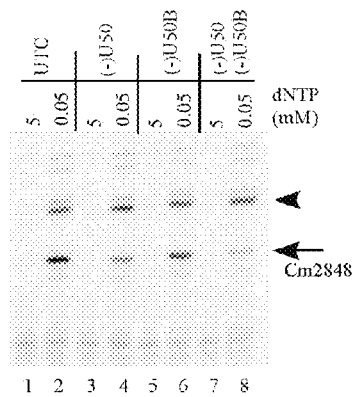
Fig 31
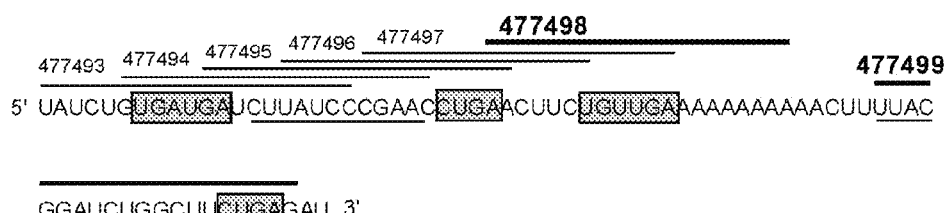

In vivo Reduction of U16 and U50 snoRNA in various tissues

Fig-50
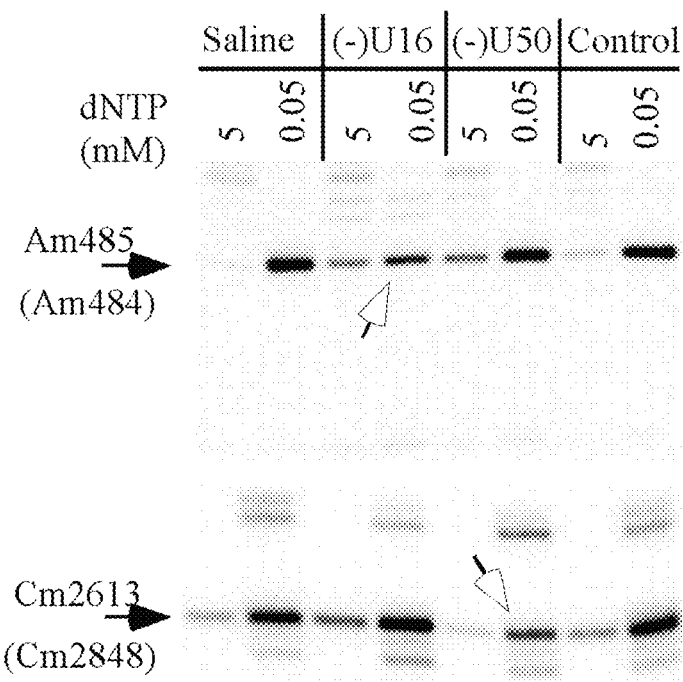
Fig-51
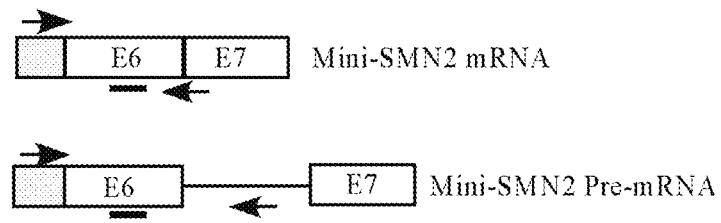
Fig-52      Fig-53
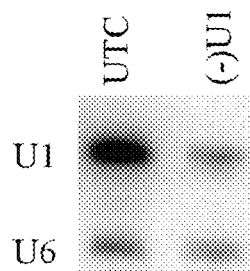 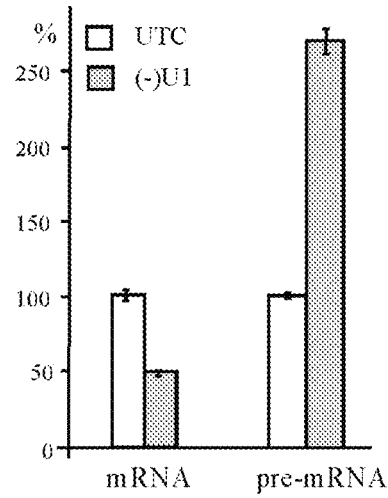

US 9,845,467 B2

COMPOUNDS AND METHODS FOR MODULATING TARGET NUCLEAR AND SUB-NUCLEAR NUCLEIC ACID MOLECULES IN CELLS AND ANIMALS

STATEMENT OF GOVERNMENT SUPPORT

This invention was made with government support under CA013106 awarded by The National Institutes of Health. The government has certain rights in the invention.

SEQUENCE LISTING

The present application is being filed along with a Sequence Listing in electronic format. The Sequence Listing is provided as a file entitled CORE0093USC1SEQ_ST25.txt, created on Mar. 3, 2016 and is 32 Kb in size. The information in the electronic format of the sequence listing is incorporated herein by reference in its entirety.

BACKGROUND

Antisense compounds have been shown to be effective for modulating the amount, activity, and/or function of cellular target nucleic acids. Certain chemical modifications have been incorporated into antisense oligonucleotides to enhance one or more properties of such antisense compounds. In certain instances, such chemically modified oligonucleotides have been shown to possess desirable characteristics compared to unmodified oligonucleotides, such as improved affinity for target and/or resistance to degradation. Chemically modified antisense oligonucleotides have been shown to have value as research tools, diagnostic reagents, and therapeutic agents, depending on the target nucleic acid and chemical modifications.

Certain nucleic acid molecules have been shown to localize to cellular sub-organelles. Certain such nucleic acid molecules are RNA molecules, including non-coding RNA molecules. For example, small nucleolar RNA molecules (snoRNA) localize to the nucleolus inside the nucleus of eukaryotic cells. In certain instances, such snoRNA have been shown to be associated with precursors of ribosomal RNA (rRNA). Accordingly, certain snoRNAs have been reported to be involved in nucleotide modification and processing of pre-rRNA. Nucleic acids have also been found in Cajal bodies within the nucleus. RNA found in Cajal bodies have been referred to as small Cajal body-specific RNA (scaRNA). Certain scaRNA have been reported to be involved in nucleotide modification of spliceosomal small nuclear RNAs (snRNAs).

Certain ncRNAs, including miRNAs and snoRNAs, are involved in biological processes, such as DNA and RNA production, and translation. However, functionalizing individual ncRNAs has lagged in time, mainly due to lack of convenient knockout or knockdown approaches in mammals. This is especially the case for ncRNAs that localize to cellular sub-organelles, such as snoRNAs and scaRNAs.

SUMMARY OF THE INVENTION

In certain embodiments, the invention provides methods of reducing the amount and/or activity of a target sub-nuclear RNA in a cell comprising contacting the cell with a modified antisense compound complementary to the target sub-nuclear RNA, wherein the contacting does not include electroporation; and thereby reducing the amount or activity of the target sub-nuclear RNA in the cell. In certain such methods, the modified antisense compound is an oligomeric compound comprising an oligonucleotide consisting of 10 to 30 linked nucleosides, wherein the oligonucleotide comprises: a 5'-region consisting of 1 to 7 modified nucleosides; a 3'-region consisting of 1 to 7 modified nucleosides; and a central region consisting of 5 to 28 deoxyribonucleosides or DNA-like nucleosides. In certain embodiments, each modified nucleoside of the 5'-region and each modified nucleoside of the 3' region comprises a modified sugar moiety. In certain embodiments, the modification of at least one modified sugar moiety is selected from among: 2'-MOE, 2'-OMe, 2'-F, and a bicyclic sugar moiety.

In certain such methods, the target sub-nuclear RNA is a snoRNA. In certain methods, the target sub-nuclear RNA is a scaRNA. In certain embodiments, the target sub-nuclear RNA derives from a host RNA. In certain such embodiments, the amount and activity of the host RNA are essentially unchanged.

In certain embodiments, the invention provides methods, wherein a reduced activity of a target sub-nuclear RNA results in a change in the processing of at least one object RNA. In certain embodiments, the processing of at least one object RNA comprises a modulation of methylation of at least one object RNA. In certain embodiments, at least one object RNA is a ribosomal RNA. In certain embodiments, at least one object RNA is an mRNA.

In certain embodiments, the cell is a cancer cell. In certain embodiments, modulation of the sub-nuclear nucleic acid results in a reduction of cell viability and/or a change in cell cycling. In certain such embodiments the result is a delay in progression to S-phase.

In certain embodiments, the cell is in vitro. In certain embodiments, the cell is in an animal, including, but not limited to, a human.

In certain embodiments, such methods are used for functionalizing the target sub-nuclear RNA.

In certain embodiments, the present invention provides a pharmaceutical composition comprising a modified antisense compound complementary to a target sub-nuclear RNA and at least one diluent or carrier.

In certain embodiments, the modified antisense compound is an oligomeric compound comprising an oligonucleotide consisting of 10 to 30 linked nucleosides, wherein the oligonucleotide comprises: a 5'-region consisting of 1 to 7 modified nucleosides; a 3'-region consisting of 1 to 7 modified nucleosides; and a central region consisting of 5 to 28 deoxyribonucleosides, or DNA-like nucleosides.

In certain embodiments, the invention provides methods of administering such a pharmaceutical composition to an animal, including, but not limited to a human. The pharmaceutical composition may be administered systemically, for example by injection, for example, sub-cutaneous injection.

BRIEF DESCRIPTION OF THE FIGURES

FIG. 1 shows composition of the 5-10-5 RNA-DNA chimeric ASOs described in Example 1. All nucleotides are linked by phosphorothioate backbone (PS). "R" and "d" mean ribonucleoside and deoxyribonucleoside, respectively. "m" means 2'-O-methyloxyethyl nucleoside (MOE).

FIG. 27 shows U50 snoRNA is present in an intron of SNHG5 non-protein coding gene, as described in Example 11. A U50 snoRNA isoform (U50B) is embedded in a second intron.

FIG. 28 shows a sequence comparison of U50 and U50B snoRNA, as described in Example 10.

FIG. 29 shows results of a Northern hybridization of U50 and U50B snoRNAs described in Example 11.

FIG. 30 compares the sequence of ASO477499 to U50 and U50B snoRNA, as described in Example 11. The snoRNA sequences are in bold. The ribonucleotides in the chimeric ASOs are shown in upper case and DNA nucleotides in lower case.

FIG. 31 shows ASOs targeting U50 snoRNA, as described in Example 11. The C and D motifs are boxed. The sequences involved in guiding rRNA modification are underlined. The positions of active ASOs are indicated with thick lines.

FIG. 32 shows results of an assay for U50 (ASO477499) or its isoform U50B snoRNA (ASO485259) described in Example 11.

FIG. 33 shows results from an assay for depletion of U50 or U50B snoRNA and its effect on the methylation guided by this RNA described in Example 12. The targeted modification site is indicated, and a neighboring potential modification site is marked with an arrowhead.

FIG. 50 shows reduction of snoRNAs in vivo decreased the levels of rRNA methylation targeted by the snoRNA. Total RNA used in panel i was pooled for each group, and subjected to primer extension analysis to detect rRNA methylation at positions targeted by U16 snoRNA (Am485 in 18S rRNA) or U50 snoRNA (Cm2613 in 28S rRNA). Open arrows indicate the reduced methylation level which is reflected by reduced signal strength at 0.05 mM dNTP concentration, as compared with control samples. The modified nucleotides are numbered with mouse rRNA. The equivalent positions in human rRNAs are shown in parentheses.

FIG. 51 shows positions of primer probe sets used in panel b. Exons (E) are shown in boxes. Primer positions are indicated using arrows. The probe position in exon 6 is marked with a bar.

FIG. 52 shows results of an assay with U1 specific ASO described in Example 21.

FIG. 53 shows ASO-mediated U1 depletion impaired pre-mRNA splicing, as described in Example 21.

DETAILED DESCRIPTION OF THE INVENTION

Figure 2:
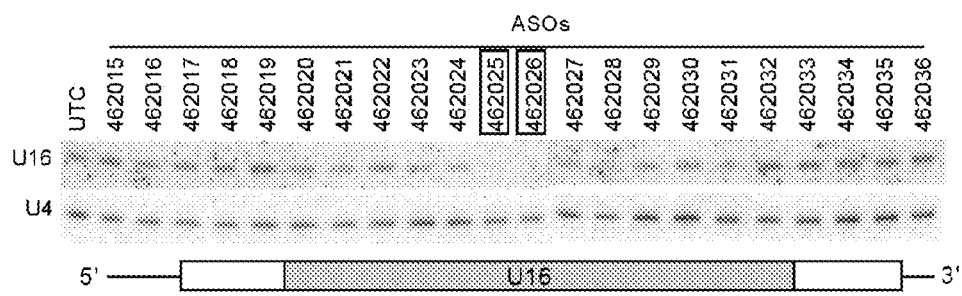
FIG. 2 shows active ASOs described in Example 1. UTC=untreated cells. Lower panel shows U16 snoRNA regions targeted by the ASOs. The gray box indicates coding region of the snoRNA, whereas the white boxes represent the junctions between the coding region and flanking sequences. The thin line indicates flanking sequences.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising modifications at the 2'-position, the 5'-position and/or the 4'-position. Certain substituted sugar moieties are bicyclic sugar moieties.

As used herein, "MOE" means —OCH$_2$CH$_2$OCH$_3$.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides."

As used herein, "nucleobase" means group of atoms that can be linked to a sugar moiety to create a nucleoside that is capable of incorporation into an oligonucleotide, and wherein the group of nucleobase atoms are capable of bonding with a complementary nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not an unmodified nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, the term "double-stranded" in reference to a compound or composition means two separate oligomeric compounds that are hybridized to one another. Double-stranded oligomeric compounds may include one or more non-hybridizing nucleosides at one or both ends of one or both strands (overhangs) and/or one or more internal non-hybridizing nucleosides (mismatches) provided there is sufficient complementarity to maintain hybridization under relevant conditions. In certain embodiments, a double-stranded oligomeric compound may become single-stranded after contacting a cell or enzyme within a cell.

As used herein, the term "self-complementary" or "hair-pin" in reference to an oligomeric compound means a single oligomeric compound that comprises a stable duplex region formed by the oligomeric compound hybridizing to itself. In certain embodiments, the stable duplex region of a hair-pin oligomeric compound comprises at least 5 contiguous paired nucleobases. In certain embodiments, the stable duplex region of a hair-pin oligomeric compound comprises at least 6 contiguous paired nucleobases. In certain embodiments, the stable duplex region of a hair-pin oligomeric compound comprises at least 7 contiguous paired nucleobases. In certain embodiments, the duplex region of a hair-pin compound constitutes ≥70% of the total number of nucleobases of the hair-pin compound.

As used herein, the term "single-stranded" means an oligomeric compound that is not hybridized to its complement and that is not a hair-pin oligomeric compound. Typically, single-stranded compounds are capable of binding to their complementary strands to become double-stranded or partially double-stranded compounds.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and clearance.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is at least partially complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means an activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes, ultimately resulting in an antisense activity.

As used herein, "sub-nuclear RNA" means an RNA molecule that is found in a sub-organelle within the nucleus of a cell. In certain embodiments, sub-nuclear RNAs are found in one or more of: the nucleolus, cajal bodies, nuclear speckles, and nuclear paraspeckles.

As used herein "non-coding RNA" or "ncRNA" means an RNA molecule that is not expressed. In certain embodiments, a ncRNA is a spliced intronic region of a pre-mRNA.

As used herein, "sub-nuclear ncRNA" means a non-coding RNA found within a sub-organelle of the nucleus of a cell.

As used herein, "snoRNA" means a small non-coding RNA molecule found in the nucleolus of cells.

As used herein, "nucleolus" means a non-membrane bound structure found within the nucleus of a cell comprising proteins and nucleic acids, including ribosomal DNA and precursors of rRNA.

As used herein, "scaRNA" means small non-coding RNA molecules found in cajal bodies of cells.

As used herein, "cajal body" means a non-membrane bound structure found within the nucleus of a cell comprising proteins and nucleic acids, including the protein coilin.

As used herein, "host nucleic acid" in reference to a non-coding RNA means a nucleic acid from which the non-coding RNA derived.

As used herein, "host pre-mRNA" means a pre-mRNA from which a non-coding intron is spliced.

As used herein, "host mRNA" means a mature mRNA derived from a host pre-mRNA.

As used herein, "object RNA" means an RNA molecule other than a target RNA that is affected by an antisense activity. In certain embodiments, the amount, activity, splicing, processing, and/or function of an object RNA is modulated, either directly or indirectly, by a target nucleic acid. In certain embodiments, a target nucleic acid modulates processing of an object RNA. In certain embodiments, a target nucleic acid modulates splicing of an object RNA. In certain embodiments, a target nucleic acid modulates methylation of an object RNA. In certain such embodiments, an antisense compound modulates the amount or activity of the target nucleic acid, resulting in a change in the object RNA and ultimately resulting in a change in the activity or function of the object RNA.

As used herein, "electroporation" means a process for introducing a nucleic acid into a cell using a pulse of electric current. In certain embodiments, electroporation can be used to introduce nucleic acid into the nucleus of a cell.

As used herein, "cell viability" means the ability of a cell to grow and divide. In certain embodiments it is desirable to maintain or improve cell viability. In certain embodiments, it is desirable to reduce cell viability, e.g., of cancer cells.

As used herein, "cell cycle" means a series of events leading up to cell division. Typically, cells cycle through phases. Such phases include quiescence, also called Gap 0 (abbreviated G0); interphase, divided into Gap 1 (G1), synthesis (S), and Gap 2 (G2); and division, or mitosis (M), which may be further divided into prophase, metaphase, anaphase, cytokenesis, and telophase. In certain circumstances, such cancer, cells cycle inappropriately. In certain embodiments, altering cell cycling (e.g., arresting cycling at a particular phase) is desirable.

As used herein, "mRNA" means an RNA molecule that encodes a protein.

As used herein, "pre-mRNA" means an RNA transcript that has not been fully processed into mRNA. Pre-RNA includes one or more intron.

As used herein, "pdRNA" means an RNA molecule that interacts with one or more promoter to modulate transcription.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/.

As used herein, "microRNA mimic" means an oligomeric compound having a sequence that is at least partially identical to that of a microRNA. In certain embodiments, a microRNA mimic comprises the microRNA seed region of a microRNA.

As used herein, "targeting" or "targeted to" means the association of an antisense compound to a particular target nucleic acid molecule or a particular region of nucleotides within a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another or otherwise support hybridization.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, sequence motifs and chemical modification motifs are independent of one another.

As used herein, "nucleobase-dependent chemical motif" means a motif of chemical modifications that depends on the identity of the nucleobase of a nucleoside, e.g., each pyrimidine nucleoside comprises a particular sugar moiety.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified, unless otherwise indicated. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "separate regions" means a portion of an oligonucleotide wherein the chemical modifications or the motif of chemical modifications within the portion are the same and the chemical modifications or motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "animal" means a multicellular organism of the kingdom Animalia. Animals include, but are not limited to, humans.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound.

Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$)) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

As used herein, "stable compound" and "stable structure" mean a compound that is sufficiently robust to survive isolation to a useful degree of purity from a reaction mixture, and formulation into an therapeutic agent.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, oligomeric compounds consist of an oligonucleotide. In certain embodiments, oligonucleotides comprise one or more chemical modification. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleoside comprising a modified sugar moiety. Such oligomeric compounds comprising one or more sugar-modified nucleoside may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-modified sugar moieties are referred to as 2'-modified nucleosides. In certain embodiments, a 2'-modified nucleoside comprises a 2'-substituent group selected from halo, allyl, amino, azido, SH, CN, OCN, CF$_3$, OCF$_3$, O—, S—, or N(R$_m$)-alkyl; O—, S—, or N(R$_m$)-alkenyl; O—, S— or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-modified nucleoside comprises a 2'-substituent group selected from F, NH$_2$, N$_3$, OCF$_3$, O—CH$_3$, O(CH$_2$)$_3$NH$_2$, CH$_2$—CH—CH$_2$, O—CH$_2$—CH—CH$_2$, OCH$_2$CH$_2$OCH$_3$, O(CH$_2$)$_2$SCH$_3$, O—(CH$_2$)$_2$—O—N(R$_m$)(R$_n$), —O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-modified nucleoside comprises a sugar moiety comprising a 2'-substituent group selected from F, OCF$_3$, O—CH$_3$, OCH$_2$CH$_2$OCH$_3$, 2'—O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$ and O—CH$_2$—C(=O)—N(H)CH$_3$.

In certain embodiments, a 2'-modified nucleoside comprises a sugar moiety comprising a 2'-substituent group selected from F, O—CH$_3$, and OCH$_2$CH$_2$OCH$_3$.

Certain substituted sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2',4'-(CH$_2$)$_2$-2',4'-(CH$_2$)$_3$-2',4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C (=CH₂)-2' and analogs thereof (see, published PCT International Application WO 2008/154401, published on Dec. 8, 2008).

In certain embodiments, such 4' to 2' bridges independently comprise 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)₂—, —S(=O)X—, and —N(R$_a$)—;

wherein:

x is 0, 1, or 2;

n is 1, 2, 3, or 4;

each R$_a$ and R$_b$ is, independently, H, a protecting group, hydroxyl, C₁-C₁₂ alkyl, substituted C₁-C₁₂ alkyl, C₂-C₁₂ alkenyl, substituted C₂-C₁₂ alkenyl, C₂-C₁₂ alkynyl, substituted C₂-C₁₂ alkynyl, C₅-C₂₀ aryl, substituted C₅-C₂₀ aryl, heterocycle radical, substituted heterocycle radical, heteroaryl, substituted heteroaryl, C₅-C₇ alicyclic radical, substituted C₅-C₇ alicyclic radical, halogen, OJ₁, NJ₁J₂, SJ₁, N₃, COOJ₁, acyl (C(=O)—H), substituted acyl, CN, sulfonyl (S(=O)₂-J₁), or sulfoxyl (S(=O)-J₁); and each J₁ and J₂ is, independently, H, C₁-C₁₂ alkyl, substituted C₁-C₁₂ alkyl, C₂-C₁₂ alkenyl, substituted C₂-C₁₂ alkenyl, C₂-C₁₂ alkynyl, substituted C₂-C₁₂ alkynyl, C₅-C₂₀ aryl, substituted C₅-C₂₀ aryl, acyl (C(=O)—H), substituted acyl, a heterocycle radical, a substituted heterocycle radical, C₁-C₁₂ aminoalkyl, substituted C₁-C₁₂ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH₂—O-2') BNA, (B) β-D-Methyleneoxy (4'-CH₂—O-2') BNA, (C) Ethyleneoxy (4'-(CH₂)₂—O-2') BNA, (D) Aminooxy (4'-CH₂—O—N(R)-2') BNA, (E) Oxyamino (4'-CH₂—N(R)—O-2') BNA, (F) Methyl(methyleneoxy) (4'-CH(CH₃)—O-2') BNA (also referred to as constrained ethyl or cEt), (G) methylene-thio (4'-CH₂—S-2') BNA, (H) methylene-amino (4'-CH2-N(R)-2') BNA, (I) methyl carbocyclic (4'-CH₂—CH(CH₃)-2') BNA, and (J) propylene carbocyclic (4'-(CH₂)₃-2') BNA as depicted below.

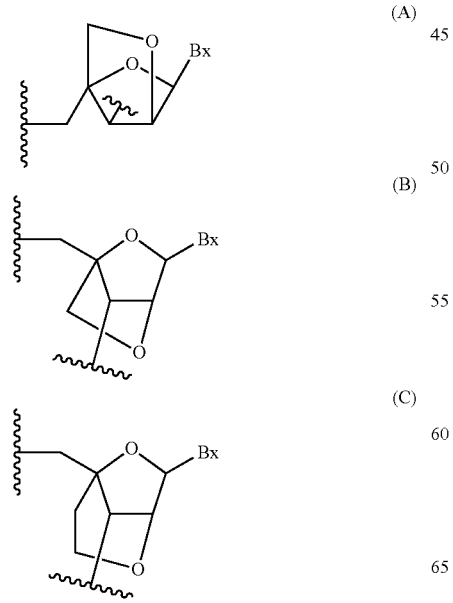

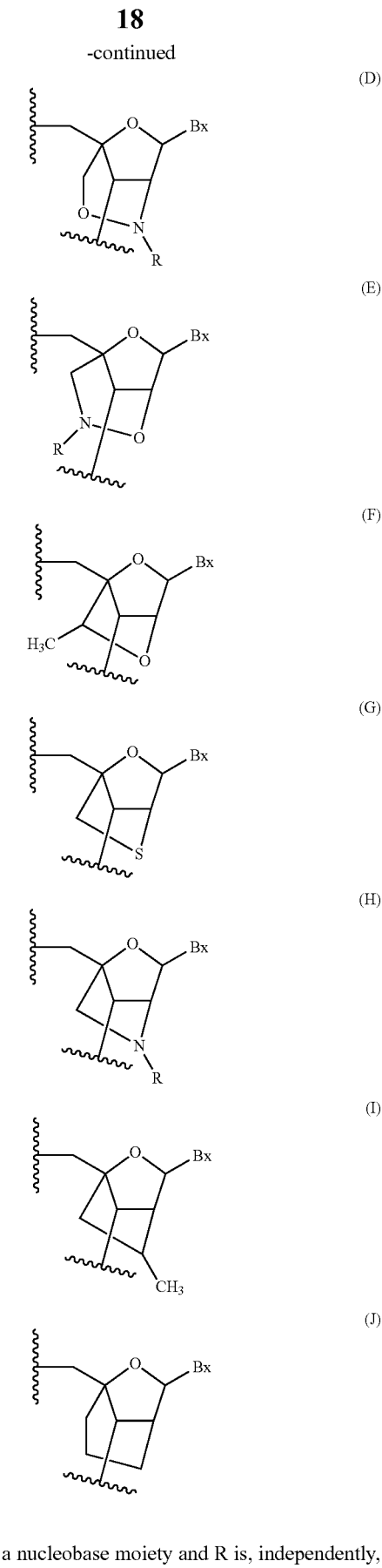

wherein Bx is a nucleobase moiety and R is, independently, H, a protecting group, or C₁-C₁₂ alkyl.

In certain embodiments, bicyclic nucleosides have Formula I:

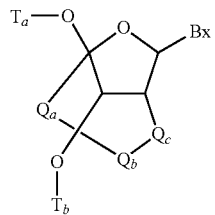

I wherein:
Bx is a nucleobase moiety;
-Q$_a$-Q$_b$-Q$_c$- is —CH$_2$—N(R$_c$)—CH$_2$—, —C(=O)—N(R$_c$)—CH$_2$—, —CH$_2$—O—N(R)—, —CH$_2$—N(R)—O—, or —N(R$_c$)—O—CH$_2$;
R$_c$ is C$_1$-C$_{12}$ alkyl or an amino protecting group; and
T$_a$ and T$_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

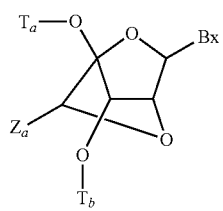

II wherein:
Bx is a nucleobase moiety;
T$_a$ and T$_b$ are each, independently, H, a hydroxyl protecting group, a conjugate group, a reactive phosphorus group, a phosphorus moiety, or a covalent attachment to a support medium;
Z$_a$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol, or substituted thio.

In certain embodiments, each of the substituted groups is, independently, mono or poly substituted with substituent groups independently selected from halogen, oxo, hydroxyl, OJ$_c$, NJ$_c$J$_d$, SJ$_c$, N$_3$, OC(=X)J$_c$, and NJ$_e$C(=X)NJ$_c$J$_d$, wherein each J$_c$, J$_d$, and J$_e$ is, independently, H, C$_1$-C$_6$ alkyl, or substituted C$_1$-C$_6$ alkyl and X is O or NJ$_c$.

In certain embodiments, bicyclic nucleoside have Formula III:

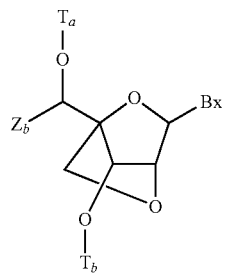

III wherein:
Bx is a nucleobase moiety;
T$_a$ and T$_b$ are each, independently, H, a hydroxyl protecting group, a conjugate group, a reactive phosphorus group, a phosphorus moiety, or a covalent attachment to a support medium;
Z$_b$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, or substituted acyl (C(=O)—).

In certain embodiments, bicyclic nucleoside having Formula IV:

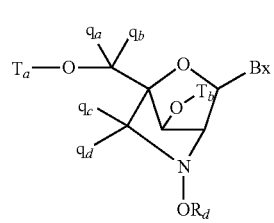

IV wherein:
Bx is a nucleobase moiety;
T$_a$ and T$_b$ are each, independently H, a hydroxyl protecting group, a conjugate group, a reactive phosphorus group, a phosphorus moiety, or a covalent attachment to a support medium;
R$_d$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, or substituted C$_2$-C$_6$ alkynyl;
each q$_a$, q$_b$, q$_c$ and q$_d$ is, independently, H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, or substituted C$_2$-C$_6$ alkynyl, C$_1$-C$_6$ alkoxyl, substituted C$_1$-C$_6$ alkoxyl, acyl, substituted acyl, C$_1$-C$_6$ aminoalkyl, or substituted C$_1$-C$_6$ aminoalkyl;

In certain embodiments, bicyclic nucleoside having Formula V:

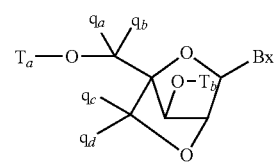

V wherein:
Bx is a nucleobase moiety;
T$_a$ and T$_b$ are each, independently, H, a hydroxyl protecting group, a conjugate group, a reactive phosphorus group, a phosphorus moiety, or a covalent attachment to a support medium;
q$_a$, q$_b$, q$_c$ and q$_f$ are each, independently, hydrogen, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_1$-C$_{12}$ alkoxy, substituted C$_1$-C$_{12}$ alkoxy, OJ$_j$, SJ$_j$, SOJ$_j$, SO$_2$J$_j$, NJ$_j$J$_k$, N$_3$, CN, C(=O)OJ$_j$, C(=O)NJ$_j$J$_k$, C(=O)J$_j$, O—C(=O)NJ$_j$J$_k$, N(H)C(=NH)NJ$_j$J$_k$, N(H)C(=O)NJ$_j$J$_k$ or N(H)C(=S)NJ$_j$J$_k$;
or q$_e$ and q$_f$ together are =C(q$_g$)(q$_h$);
q$_g$ and q$_h$ are each, independently, H, halogen, C$_1$-C$_{12}$ alkyl, or substituted C$_1$-C$_{12}$ alkyl.

In certain embodiments, bicyclic nucleoside having Formula VI:

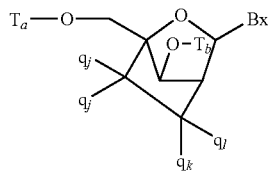

wherein:

Bx is a nucleobase moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$, or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl, or substituted $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

The synthesis and preparation of many bicyclic sugar moieties and bicyclic nucleosides has been described. For example, synthesis of methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226. See also, Kumar et al., *Bioorg. Med. Chem. Lett.*, 1998, 8, 2219-2222; Wengel et al., WO 99/14226; Singh et al., *J. Org. Chem.*, 1998, 63, 10035-10039 (including synthesis of 2'-amino-BNA and 2'-amino- and 2'-methylamino-BNA').

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

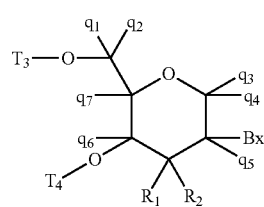

wherein independently for each of said at least one tetrahydropyran nucleoside analog of Formula X:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and 0-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared a racemic mixture, as separate enantomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), □ or □ such as for sugar anomers, or as (D) or (L) such as for amino acids et al. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified sugar. In certain embodiments, chemically modified oligonucleotides comprise one or more modified nucleobase. In certain embodiments, chemically modified oligonucleotides comprise one or more modified internucleoside linkage. In certain embodiments, the chemically modifications (sugar modifications, nucleobase modifications, and/or linkage modifications) define a pattern or motif. In certain embodiments, the patterns of chemically modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemically modifications to the nucleobases independent of the sequence of nucleobases).

Certain Sugar Motifs

In certain embodiments, oligonucleotides comprise modified sugar moieties arranged along the oligonucleotide or region thereof in a defined pattern or sugar modification motif. In certain such embodiments, the oligonucleotides of the present invention comprise a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein the sugar moieties of the nucleosides of each of the wings are different from the sugar moieties of the nucleosides of the gap. Typically, the sugar moieties within each of the two wings are the same as one another and the sugar moieties within the gap are the same as one another. In certain embodiments, the sugar moieties of the two wings are the same as one another (symmetric gapmer). In certain embodiments, the sugar moieties in the 5'-wing are different from the sugar moieties in the 3'-wing (asymmetric gapmer).

In certain embodiments, the nucleosides of the 5'-wing and the nucleosides of the 3'-wing are sugar modified nucleosides. In certain embodiments, the nucleosides of the gap comprise unmodified β-D-2'-deoxyribonucleosides (i.e., the sugar moiety is the unmodified deoxyfuranosyl of DNA). In certain embodiments, the wings are each from 1 to 10 nucleosides in length. In certain embodiments, the wings are each from 1 to 5 nucleosides in length. In certain embodiments, the gap is from 5 to 25 nucleosides in length. In certain embodiments, the gap is from 8 to 18 nucleosides in length. In certain embodiments, gapmers may be described using the following formula:

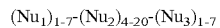

wherein Nu$_1$, Nu$_2$, and Nu$_3$ are nucleosides, wherein the sugar moieties of the Nu$_2$ nucleosides are different from the sugar moieties of the Nu$_1$ and Nu$_3$ nucleosides and wherein the sugar moieties of the Nu$_1$ nucleosides and the Nu$_3$ nucleosides may be the same or different from one another.

In certain embodiments, gapmer oligonucleotides or regions can have any of the following, non-limiting list of numbers of nucleosides in the three regions (where the first number represents the number of nucleosides in the 5'-wing, the second number represents the number of nucleosides in the gap, and the third number represents the number of nucleosides in the 3'-wing): 1-18-1; 1-18-2; 2-18-1; 2-18-2; 1-17-1; 1-17-2; 2-17-1; 2-17-2; 3-17-2; 3-17-1; 2-17-2; 3-17-3; 1-16-1; 2-16-2; 3-16-3; 1-16-2; 2-16-1; 2-16-3; 3-16-2; 1-15-1; 2-15-2; 3-15-3; 4-15-4; 1-15-4; 4-15-1; 2-15-3; 1-14-1; 2-14-2; 3-14-3; 4-14-4; 1-14-2; 1-14-3; 2-14-3; 1-13-1; 2-13-2; 3; 13-3; 4-13-4; 1-13-2; 2-13-3; 2-13-1; 4-13-2; 5-13-2; 5-13-4; 2-13-5; 1- 12-1; 2-12-2; 3-12-3; 4-12-4; 5-12-5; 5-12-4; 4-12-5; 3-12-5; 5-12-3; 1-11-1; 2-11-2; 3-11-3; 4-11-4; 5-11-5; 6-11-6; 5-11-4; 4-11-5; 6-11-3; 3-11-5; 1-10-1; 2-10-2; 3-10-3; 4-10-4; 5-10-5; 6-10-6; 6-10-5; 5-10-6; 5-10-4; 4-10-5; 5-10-3; 3-10-5; 4-10-3; 3-10-4; 2-10-5; 5-10-2; 1-9-1; 2-9-2; 3-9-3; 4-9-4; 5-9-5; 6-9-6; 6-9-5; 5-9-6; 6-9-4; 4-9-6; 5-9-4; 4-9-5; 5-9-3; 3-9-5; 3-9-4; 4-9-3; 1-8-1-; 2-8-2; 3-8-3; 4-8-4; 5-8-5; 6-8-6; 6-8-5; 6-8-4; 6-8-3; 5-8-6; 4-8-6; 3-8-6; 5-8-4; 5-8-3; 5-8-2; 4-8-2; 4-8-5; 4-8-3; 4-8-2; 1-7-1; 2-7-2; 3-7-3; 4-7-4; 5-7-5; 6-7-6; 1-6-1; 2-6-2; 3-6-3; 4-6-4; 5-6-5; and 6-6-6.

In certain embodiments, the sugar moieties of the nucleosides of one or both wings are modified sugar moieties. In certain such embodiments, the modified nucleosides of the 5'-wing comprise modified sugar moieties selected from any of the modified sugar moieties described herein. In certain such embodiments, the modified nucleosides of the 3'-wing comprise modified sugar moieties selected from any of the modified sugar moieties described herein. In certain embodiments, the nucleosides of the gap are unmodified 2'-deoxynucleosides.

In certain embodiments, the sugar moieties of the wings are sugar moieties that adopt a 3'-endo or southern conformation. In certain such embodiments, the sugar moieties of the gap are sugar moieties that adopt a 2'-endo or northern conformation. In certain embodiments, the sugar moieties of both the 3'-wing and the 5'-wing comprise a 2'-MOE and the sugars of the nucleosides of the gap are unmodified deoxyribofuranosyl.

In certain embodiments, one or both wing region comprises more than one type of sugar modification. For example, in certain embodiments, the 5'-wing region comprises two different types of sugar modifications, the gap region comprises nucleosides having a different type of sugar moieties, and the 3' wing region comprises two different types of sugar modifications. Such a gapmer may be described using the earlier described convention, for example a (1-2)-14-(2-1) means that the 5'-wing comprises 3 nucleosides, wherein the 5' terminal nucleoside has a sugar modification of a first-type and the next two are of a different type, but the same as one another; the gap is 14 nucleosides in length; and the 3' wing comprises 3 nucleosides wherein the sugar moiety of the terminal nucleoside differs from that of the previous 2. Such gapmers are referred to herein as "mixed wing gapmers." Such mixed wing gapmers may have more than one type of sugar modification at the 5' wing (5'-mixed-wing gapmers); the 3' wing (3'-mixed wing gapmers); or both the 3'-wing and the 5'-wing (5'/3' mixed wing gapmers).

In certain embodiments, the oligonucleotides of the present invention comprise a region having an alternating sugar motif, which comprises at least four separate regions of modified nucleosides in a pattern $(AB)_nA_m$ where A represents a region of nucleosides having a first type of sugar modification (including no modification); B represent a region of nucleosides having a different type of sugar modification (including no modification); n is 2-15; and m is 0 or 1. Thus, in certain embodiments, alternating motifs include 4, 5, 6, 7, 8, 9, 10, 11, 12, 13, 14, 15, 16, 17, 18, 19, or 20 or more alternating regions. In certain embodiments, each A region and each B region independently comprises 1-4 nucleosides.

In certain embodiments, the oligonucleotides of the present invention comprise a region that is fully sugar modified, meaning that each nucleoside is a sugar modified nucleoside. The modifications of the nucleosides of a fully modified oligomeric compound may all be the same or one or more may be different from one another.

In certain embodiments, the oligonucleotides of the present invention comprise a region that is uniformly sugar modified, which means that each nucleoside within that region comprises the same sugar modification.

In certain embodiments, the sugar motif is a nucleobase-dependent chemical motif. For example, in certain embodiments, each pyrimidine in an oligonucleotide comprises the same sugar modification, independent of its position within the oligonucleotide. In certain embodiments, each purine has the same sugar modification as one another.

In certain embodiments, oligonucleotides of the present invention do not have nucleobase-dependent chemical motifs. Accordingly, modifications are designed based on position, rather than nucleobase identity. In certain such embodiments, oligonucleotides comprise at least two nucleosides having the same nucleobase and different sugar modifications. In certain embodiments, oligonucleotides not having a nucleobase-dependent chemical motif may nevertheless comprise nucleosides having the same nucleobase having the same sugar modification. In certain such embodiments, each nucleoside having the same nucleobase might, by chance, have the same sugar modification (e.g., an antisense sequence designed as a gapmer wherein each cytosine is in one of the wing regions and thus each has the same modification).

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides of the present invention comprise a region having an alternating internucleoside linkage motif. In certain embodiments, oligonucleotides of the present invention comprise a region of fully modified internucleoside linkages. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly phosphorothioate. In certain embodiments, each internucleoside linkage of the oligonucleotide is selected from phosphodiester and phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least block of at least 6 consecutive phosphorothioate internucleoside linkages. In certain embodiments, the oligonucleotide comprises at least block of at least 8 consecutive phosphorothioate internucleoside linkages. In certain embodiments, the oligonucleotide comprises at least block of at least 10 consecutive phosphorothioate internucleoside linkages. In certain embodiments, the oligonucleotide comprises at least block of at least 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified (fully modified nucleobase motif). In certain embodiments, nucleobase modifications are uniform throughout an oligonucleotide. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uricil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methyl state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gaped sugar motif may be modified or unmodified and may or may not follow the modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create or to describe a variety of oligonucleotides, such as those provided in the non-limiting table below.

| Overall Length | Sugar Motif | Internucleoside Linkage Motif | Nucleobase Mod. Motif |
|---|---|---|---|
| 20 | 5-10-5 gapmer w/2'MOE wings and unmodified deoxyribose gap | uniform PS | uniform unmodified |
| 20 | 5-10-5 gapmer w/2'MOE wings and unmodified deoxyribose gap | 2-14-2 gapmer: PO in wings and PS in gap | uniform unmodified |
| 20 | 5-10-5 gapmer w/BNA wings and unmodified deoxyribose gap | uniform PS | uniform unmodified; all C's are 5-meC |
| 20 | 5-10-5 asymmetric gapmer w/2'MOE in 3'-wing; BNA in 5'-wing; and unmodified deoxyribose gap | uniform PS | uniform unmodified; no Cs are 5-meC) |
| 18 | Uniform 2'MOE | uniform PS | uniform unmodified; at least one nucleobase is a 5-meC |
| 16 | 2-12-2 gapmer w/BNA in each wing and unmodified deoxyribose gap | uniform PS | uniform unmodified |
| 16 | 2-12-2 gapmer w/2'-MOE in each wing and unmodified deoxyribose gap | uniform PS | uniform unmodified |
| 14 | 2-10-2 gapmer w/2'-MOE in each wing and unmodified deoxyribose gap | All PS or PO | uniform unmodified |
| 14 | 2-10-2 gapmer w/2'-BNA in each wing and unmodified deoxyribose gap | uniform PS | uniform unmodified |
| 16 | 2-12-2 gapmer w/BNA in 5'-wing; 2'-MOE in 3'-wing; and unmodified deoxyribose gap | uniform PS | uniform unmodified |
| 16 | 2-12-2 gapmer w/BNA in 5'-wing; mixed 2'-MOE and BNA in 3'-wing; and unmodified deoxyribose gap | uniform PS | uniform unmodified |
| 22 | 5-12-5 gapmer w/BNA in 5'-wing; mixed 2'-MOE and BNA in 3'-wing; and unmodified deoxyribose gap | uniform PS | uniform unmodified |

| Overall Length | Sugar Motif | Internucleoside Linkage Motif | Nucleobase Mod. Motif |
|---|---|---|---|
| 16 | (1-2)-10-(2-1) mixed wing gapmer: MOE-BNA-DNA-BNA-MOE | uniform PS | uniform unmodified |

The above table is intended only to illustrate and not to limit the various combinations of the parameters of oligonucleotides of the present invention. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutozone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

Certain Antisense Activities and Mechanisms

Antisense activities include, but are not limited to a change in the amount, expression, and/or function of a target nucleic acid. Antisense activity may be mediated by any of a variety of mechanisms. In certain embodiments, hybridization of the antisense compound results in cleavage of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings. Another example of antisense mechanisms that may result in cleavage of a target nucleic acid includes, without limitation RNAi mechanisms, which utilize the RISC pathway. Antisense compounds that elicit cleavage at least in part via RNAi mechanisms include short-interfering RNAs (siRNA), which are typically double-stranded, and single-stranded RNAi compounds (ssRNAi). Such antisense compounds typically comprise one or more RNA nucleosides or modified nucleosides that are RNA-like. In certain embodiments, oligomeric compounds of the present invention are RNAi compounds. In certain embodiments, oligomeric compounds of the present invention are ssRNA compounds.

In certain embodiments, oligomeric compounds of the present invention are paired with a second oligomeric compound to form an siRNA. In certain such embodiments, the second oligomeric compound is also an oligomeric compound of the present invention. In certain embodiments, the second oligomeric compound is any modified or unmodified nucleic acid. In certain embodiments, the oligomeric compound of the present invention is the antisense strand in an siRNA compound. In certain embodiments, the oligomeric compound of the present invention is the sense strand in an siRNA compound.

Certain antisense mechanisms typically do not necessarily promote immediate enzyme mediated cleavage of the target nucleic acid, but nonetheless disrupt or alter its function or activity. In certain embodiments, antisense compounds are microRNA mimics, which involve certain components of the RISC pathway, but typically result in sequestration, rather than immediate cleavage of the target nucleic acid. Certain antisense compounds exert antisense activity by occupancy (i.e., presence of the antisense compound hybridized to the target nucleic acid results in a change in the function of the target nucleic acid and/or in the way the target nucleic acid interacts with another molecule). For example, in certain embodiments, antisense compounds hybridize to a pre-mRNA and alter processing of the pre-mRNA. For example, in certain embodiments, the antisense compound modulates polyadenylation and/or addition of the 5'-cap. In certain such embodiments, the resulting mRNA with altered or absent polyadenylation or 5-cap may be less stable than the non-modulated form. Thus, the antisense activity may ultimately result in the generation of a mature mRNA that is degraded more quickly than one in which such functions has not been altered.

In certain embodiments, the antisense compound alters splicing of the pre-mRNA, resulting in a differently spliced mature mRNA. Modulation of splicing may result in a change in the inclusion or exclusion of a portion of pre-mRNA (intron, exon, alternate intron, or alternat exon) in the mature mRNA compared to that of a mature mRNA in the absence of the antisense compound. Such splice-altered mature mRNA may have different stability characteristics. Thus, the splice-altered mRNA may degrade more or less quickly resulting in a corresponding increase or decrease in the protein expressed from the mature mRNA. In certain embodiments, a splice-altered mature mRNA may encode a different protein than the unaltered mRNA. In certain embodiments, an antisense compound alters the ratio of splice variants of a protein product, wherein both splice variants are present in the absence of the antisense compound, but at different amounts. In certain embodiments, an antisense compound alters splicing ultimately resulting in a protein product that is not present in the absence of the antisense compound.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA (ncRNA). In certain such embodiments, the target non-coding RNA is selected from: a long-non-coding RNA, a short non-coding RNA, an intronic RNA, a snoRNA, a scaRNA, a microRNA (including pre-microRNA and mature microRNA), a ribosomal RNA (rRNA), and promoter directed RNA. In certain embodiments, a target nucleic acid is a non-coding RNA other than a microRNA. In certain embodiments, the target nucleic acid encodes a protein. In certain such embodiments, the target nucleic acid is selected from: an mRNA and a pre-mRNA, including intronic, exonic and untranslated regions thereof. In certain embodiments, antisense compounds are at least partially complementary to more than one target nucleic acid. For example, oligomeric compounds of the present invention may mimic microRNAs, which typically bind to multiple targets.

In certain embodiments, target nucleic acids are localized in an organelle within a cell. In certain embodiments, a target nucleic acid is a nuclear retained RNA. In certain such embodiments, a target nucleic acid is a short-nuclear RNA (snRNA). In certain embodiments, target nucleic acids are localized in a sub-organelle within an organelle in a cell. In certain embodiments, target nucleic acids are localized in a sub-organelle within the nucleus of a cell. In certain embodiments, target nucleic acids are localized within a nucleolus. In certain embodiments, target nucleic acids are localized within a cajal body. In certain embodiments, a target nucleic acid is a snoRNA. In certain embodiments, a target nucleic acid is a scaRNA.

In certain embodiments, a target nucleic acid is a snoRNA. Hundreds of eukaryotic snoRNAs have been identified. Certain snoRNAs have been divided into one of two major groups: C/D box snoRNAs and H/ACA box snoRNAs. The present invention provides antisense compounds targeting snoRNAs, including, but is not limited to, antisense compounds targeting to C/D box snoRNAs and/or H/ACA box snoRNAs. In certain instances, snoRNAs guide site-specific nucleotide modifications in rRNAs and/or other ncRNAs. Generally, C/D snoRNA mediate 2'-O-methylation and H/ACA snoRNA mediate pseudouridylation ($\Psi$), through base-pairing with a substrate RNA. The mechanisms of RNA-guided RNA modification are conserved in eukaryotes, and similar machineries also exist in archae. Although certain yeast snoRNAs have been characterized through genetic knockout, the functions of many snoRNAs in other organisms have not been verified. This is particularly problematic since many snoRNAs are species specific. Certain human snoRNAs have been predicted to guide modifications in rRNAs and ncRNAs, including snRNAs, but in certain instances, those predictions have not been experimentally confirmed. In addition, ~110 in ~360 human snoRNAs have no identified target sites in rRNAs or snRNAs, suggesting those snoRNAs have other roles, e.g., in modulating expression of protein-coding genes. Indeed, a mammalian snoRNA (HBII52) has been shown to regulate alternative splicing, and snoRNA-originated miRNAs have been identified. In certain instances, the snoRNA-related machinery has been implicated in human diseases, e.g., Dyskeratosis congenita and Prader-Willi syndrome, thus it is important to functionalize snoRNAs, and to manipulate their expression for therapeutic purposes.

Certain Mechanisms/Uses

In certain embodiments, the present invention provides compositions and methods for reducing the amount or activity of a target nucleic acid. In certain embodiments, the invention provides compositions comprising antisense compounds and methods. In certain embodiments, the invention provides compositions comprising antisense compounds and methods based on activation of RNase H. In certain embodiments, the invention provides RNAi compounds and methods. In certain embodiments, the invention provides antisense compounds and methods that do not depend on the RNAi pathway. In certain embodiments, the invention provides antisense compounds based on occupation of the target nucleic acid.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human. In certain embodiments, the cell is a liver cell. In certain embodiments, the cell is an epithelial cell. In certain embodiments, the cell is a cancer cell.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intraventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

In certain embodiments, antisense compounds of the present invention modulate the amount, activity, and/or function of a target nucleic acid in a cell. In certain such embodiments, the target nucleic acid is an snRNA. In certain embodiments, the target nucleic acid is a target sub-nuclear nucleic acid. In certain embodiments, the target nucleic acid is a target sub-nuclear nucleic acid. In certain such embodiments, the target sub-nuclear nucleic acid is a snoRNA, including, but not limited to C/D box snoRNAs and H/ACA box snoRNAs. In certain such embodiments, antisense compounds reduce the amount, activity, and/or function of a target snoRNA. In certain embodiments, such antisense compounds are used to functionalize the target snoRNA. Such functionalization may be performed in vitro and/or in vivo.

In certain embodiments, antisense compounds are used to modulate an object nucleic acid. In certain embodiments, antisense compounds are used to functionalize an object nucleic acid. In certain embodiments, the object nucleic acid is a rRNA. In certain embodiments, antisense compounds of the present invention are used to disrupt normal processing of an rRNA to study rRNA function in a cell. In certain embodiments, the object nucleic acid is a pre-mRNA. In certain embodiments, inhibition of a target snoRNA results in altered splicing of an object pre-mRNA, ultimately resulting in an altered protein. In certain embodiments, an object nucleic acid is an object ncRNA. In certain embodiments, antisense compounds disrupt processing of an object ncRNA to allow functionalization of the ncRNA. Such disruption of processing of object nucleic acid may be performed in vitro and/or in vivo.

In certain embodiments, antisense compounds targeting snoRNA have therapeutic use. Certain snoRNAs have been associated with diseases. In certain embodiments, modulation of snoRNAs using antisense compounds is predicted to provide a therapeutic benefit. In certain embodiments, antisense compounds targeting snoRNAs are used to treat Dyskeratosis congenita and/or Prader-Willi syndrome. Functionalization of snoRNAs is expected to result in identification of additional specific therapeutic opportunities. Disruption of target snoRNA and/or associated object nucleic acid processing is expected to interfere with cellular function. In certain embodiments, such disruption is expected to disrupt cell cycling. In certain embodiments, disruption of object nucleic acid is used to treat cancer. In certain embodiments, antisense compounds targeting one or more snoRNA disrupt processing of rRNA, which disrupts cell cycling and/or results in toxicity to the cell. In certain instances, such disruption or toxicity ultimately resulting from the antisense compounds is desirable, for example in treating cancer.

Difficulty reducing snoRNA has been reported. Such difficulty results from several factors: 1) snoRNAs are highly structured and exist in stable snoRNP complexes; 2) many vertebrate snoRNAs are encoded in introns of host genes, and are released/processed post-transcriptionally; 3) many snoRNA genes have multi-copies or isoforms. Although over-expression of antisense RNA or dsRNA in trypanosomes has been shown to degrade snoRNAs, not all tested snoRNAs were depleted. In addition, several approaches have been tested to reduce mammalian snoRNAs, including siRNA, ribozyme, locked nucleic acid (LNA), and peptide-nucleic acid oligonucleotides. In no case was the function of the targeted snoRNA disrupted. Modulation of snoRNA using antisense compounds has been reported. For example, reduction of certain snoRNAs in cultured cells following nucleofection by electroporation has been reported. See Ideue et al., RNA 2009 15: 1578-1587, which is hereby incorporated by reference in its entirety. The present invention does not require electroporation, making it amenable to use in vivo.

In certain instances, snoRNAs are transcribed within a host nucleic acid. In certain such instances, the snoRNA is an intronic portion of a host pre-mRNA. In certain embodiments, antisense compounds of the present invention selectively reduce or inhibit a snoRNA without reducing or inhibiting the remainder of the host nucleic acid. Accordingly, in such embodiments, the amount, activity and function of the host pre-mRNA and the mRNA and protein ultimately expressed from the host pre-mRNA are essentially unchanged, relative to the reduction in the snoRNA. In certain embodiments, target snoRNA activity is reduced by at least 80% compared to untreated cells while activity of the host RNA and/or protein is reduced by less than 10%.

Certain snoRNAs share substantial identity with one another. In certain embodiments, the present invention provides antisense compounds that selectively inhibit a target snoRNA, while a non-target snoRNA is essentially unchanged. In certain such embodiments, the non-target snoRNA is a distinct isoform of the target snoRNA. In certain embodiments, the target and non-target snoRNAs share up to 70% identity. In certain embodiments, the target and non-target snoRNAs share up to 80% identity. In certain embodiments, the target and non-target snoRNAs share up to 85% identity. In certain embodiments, the target and non-target snoRNAs share up to 90% identity. In certain embodiments, the target and non-target snoRNAs share up to 95% identity. In certain embodiments, target snoRNA activity is reduced by at least 80% compared to untreated cells while activity of the non-target snoRNA is reduced by less than 10%.

In certain embodiments, the invention provides antisense compounds targeting scaRNAs, which are similar to snoRNAs, except that they are localized to cajal bodies, rather than to the nucleolus. Thus, in certain embodiments, the present invention provides antisense compounds that may be used to modulate scaRNAs and/or object nucleic acids associated with scRNAs. Such antisense compounds may be used to functionalize scaRNAs and/or object RNAs and/or may have therapeutic uses. Also similar to antisense compound to snoRNAs, in certain embodiments, antisense compounds to scaRNAs leave the amount, activity and expression of a host nucleic acid essentially unchanged.

In certain embodiments, the present invention provides methods of simultaneously reducing the amount and/or activity of more than one target sub-nuclear nucleic acid at a time. In certain embodiments, the invention provides methods of simultaneously reducing the amount and/or activity of more than one snoRNA at a time.

In certain embodiments, it is useful for inhibition of one or more target sub-nuclear nucleic acid to persist for several hours or days, for example, to allow depletion to facilitate functionalization of the target sub-nuclear nucleic acid and/or one or more object nucleic acids. A long duration of action may also be desirable in therapeutic uses. In certain embodiments, antisense compounds reduce the amount or activity of a target sub-nuclear nucleic acid more than 48 hours. In certain embodiments, antisense compounds reduce the amount or activity of a target sub-nuclear nucleic acid more than 72 hours. In certain embodiments, antisense compounds reduce the amount or activity of a target sub-nuclear nucleic acid more than 96 hours. In certain embodiments, antisense compounds reduce the amount or activity of a target sub-nuclear nucleic acid more than 100 hours.

In certain embodiments, antisense compounds complementary to a target sub-nuclear nucleic acid have unexpected potency. Since such target sub-nuclear nucleic acids are localized in sub-organelles, have secondary structure and are associated with proteins, they are expected to be difficult to inhibit. Certain antisense compounds of the present invention are surprisingly potent. In certain embodiments, the invention provides antisense compounds capable of inhibiting a target sub-nuclear nucleic acid in an animal when administered at a dose of 400 mg/kg. In certain embodiments, the invention provides antisense compounds capable of inhibiting a target sub-nuclear nucleic acid in an animal when administered at a dose of 200 mg/kg. In certain embodiments, the invention provides antisense compounds capable of inhibiting a target sub-nuclear nucleic acid in an animal when administered at a dose of 100 mg/kg. In certain embodiments, the invention provides antisense compounds capable of inhibiting a target sub-nuclear nucleic acid in an animal when administered at a dose of 50 mg/kg. In certain embodiments, the invention provides antisense compounds capable of inhibiting a target sub-nuclear nucleic acid in an animal when administered at a dose of 25 mg/kg. In certain embodiments, the invention provides antisense compounds capable of inhibiting a target sub-nuclear nucleic acid in an animal when administered at a dose of 10 mg/kg. In certain embodiments, the invention provides antisense compounds capable of inhibiting a target sub-nuclear nucleic acid in an animal when administered at a dose of 5 mg/kg. In certain embodiments, the invention provides antisense compounds capable of inhibiting a target sub-nuclear nucleic acid in an animal when administered at a dose of 1 mg/kg. In certain such embodiments, the target sub-nuclear nucleic acid is a snoRNA. In certain embodiments, the target sub-nuclear nucleic acid is a scaRNA.

Certain Pharmaceutical Compositions

In certain embodiments, the present invention provides pharmaceutical compositions comprising one or more antisense compound. In certain embodiments, such pharmaceutical composition comprises a a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water.

In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprise a polyamine compound or a lipid moiety complexed with a nucleic acid. In certain embodiments, such preparations comprise one or more compounds each individually having a structure defined by formula (I) or a pharmaceutically acceptable salt thereof,

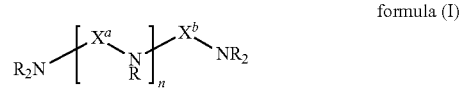

formula (I)

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (I) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety for the disclosure of lipid preparations. Certain additional preparations are described in Akinc et al., Nature Biotechnology 26, 561-569 (1 May 2008), which is herein incorporated by reference in its entirety for the disclosure of lipid preparations.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

EXAMPLES

Example 1: Antisense Inhibition of Human C/D Box Small Nucleolar (Sno) RNA U16 in Hela Cells Antisense oligonucleotides were designed targeting a U16 snoRNA nucleic acid (FIG. 1) and were tested for their effects on U16 mRNA in vitro. The chimeric antisense oligonucleotides in Table 1 were designed as 5-10-5 MOE gapmers. The gapmers were 20 nucleotides in length, wherein the central gap segment was comprised of ten 2'-deoxynucleotides and flanked on each side (in the 5' and 3' directions) by wings comprising five nucleotides each. Each nucleotide in the 5' wing segment and each nucleotide in the 3' wing segment had a 2'-MOE modified sugar moiety. The internucleoside linkages throughout each gapmer were phosphorothioate (P=S) linkages. All cytidine residues throughout each gapmer were 5-methylcytidines. Each gapmer listed in Table 1 is complementary to SEQ ID NO: 1 (complement of GENBANK Accession No. NT_010194.16 truncated from nucleotides 37585444 to 37585593).

Hela cells were cultured on 6-well plates in DMEM medium supplemented with 10% fetal calf serum and 1% penicillin/streptomycin at 37° C. in a 5% $CO_2$ incubator. Sub-confluent cells were treated with the antisense oligonucleotides at a 50 nM concentration in Opti-MEM medium containing 4 μg/mL Lipofectamine 2000 (Invitrogen, CA) for 4 hours, after which the transfection media was replaced with fresh culture medium. After a period of approximately 48 hours, RNA was isolated from the cells and the U16 snoRNA levels were determined as follows.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U16 snoRNA-specific 5'-end labeled oligonucleotide probe (5'-TTGCTCAGTAAGAATTTTCG-3', designated herein as SEQ ID NO: 2), as described in Liang et al (Mol. Cell 28: 965-977, 2007). U4 snRNA-specific probe (5'-ATTGCCA-GTGCCGACTATAT-3', designated herein as SEQ ID NO: 3) served as a control for loading. The density of the bands was scanned using an ImageJ densitometer and demonstrated that ISIS 462025 and ISIS 462026 reduced U16 snoRNA levels by 90% (FIG. 2).

TABLE 1

Chimeric antisense oligonucleotides having 5-10-5 MOE wings and deoxy gap targeted to U16 snoRNA

| Start Site | Stop Site | ISIS No. | Sequence | SEQ ID NO. |
|---|---|---|---|---|
| 1 | 20 | 462015 | ATAACCCCATATAAATGAAG | 4 |
| 9 | 28 | 462016 | CAAGCAAAATAACCCCATAT | 5 |
| 15 | 34 | 462017 | TCATTGCAAGCAAAATAACC | 6 |
| 20 | 39 | 462018 | CGACATCATTGCAAGCAAAA | 7 |
| 25 | 44 | 462019 | AATTACGACATCATTGCAAG | 8 |
| 30 | 49 | 462020 | ACGCAAATTACGACATCATT | 9 |
| 35 | 54 | 462021 | GTAAGACGCAAATTACGACA | 10 |
| 40 | 59 | 462022 | ACAGAGTAAGACGCAAATTA | 11 |
| 47 | 66 | 462023 | GCTGAGAACAGAGTAAGACG | 12 |
| 52 | 71 | 462024 | CTGTCGCTGAGAACAGAGTA | 13 |
| 57 | 76 | 462025 | GGCAACTGTCGCTGAGAACA | 14 |
| 62 | 81 | 462026 | CAGCAGGCAACTGTCGCTGA | 15 |
| 67 | 86 | 462027 | ACTGACAGCAGGCAACTGTC | 16 |
| 72 | 91 | 462028 | AGCTTACTGACAGCAGGCAA | 17 |
| 77 | 96 | 462029 | GTACCAGCTTACTGACAGCA | 18 |
| 83 | 102 | 462030 | CCTTCTGTACCAGCTTACTG | 19 |
| 88 | 107 | 462031 | GTCAACCTTCTGTACCAGCT | 20 |
| 107 | 126 | 462032 | TTGCTCAGTAAGAATTTTCG | 21 |
| 112 | 131 | 462033 | ATTTCTTGCTCAGTAAGAAT | 22 |
| 118 | 137 | 462034 | AAGGTTATTTCTTGCTCAGT | 23 |
| 123 | 142 | 462035 | ACAACAAGGTTATTTCTTGC | 24 |
| 128 | 147 | 462036 | TAATTACAACAAGGTTATTT | 25 |

Figure 3:
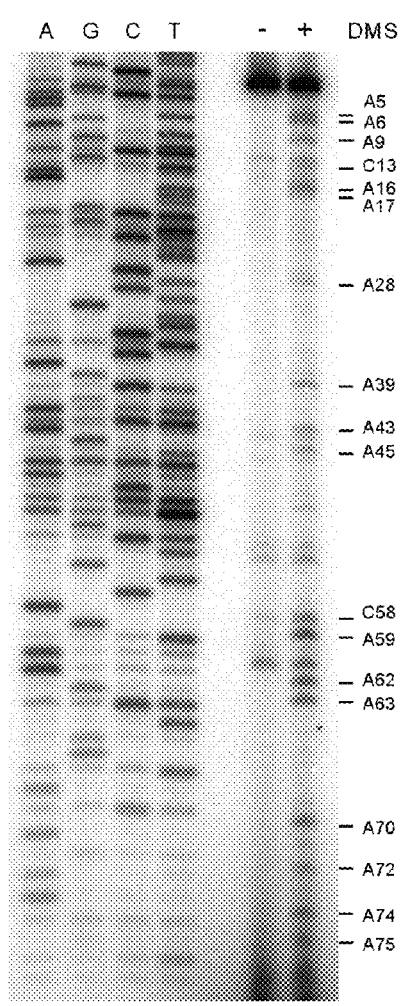
FIG. 3 shows structures for probing U16 snoRNA described in Example 1. The nucleotides accessible to DMS are identified.
Figure 4:
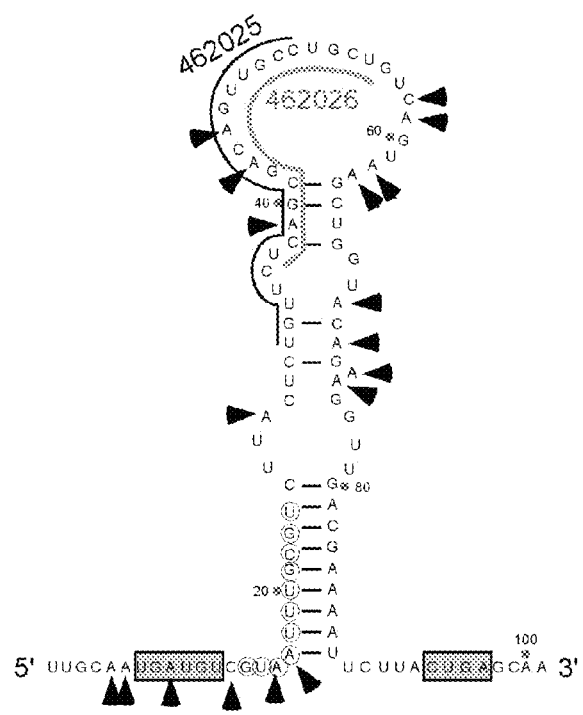
FIG. 4 shows a proposed secondary structure of U16 snoRNA described in Example 1. The structure was folded using program mFold, and refined based on the probing data in FIG. 3. The accessible nts are marked with arrowheads. The C and D motifs are boxed. The nucleotides complementary to rRNA for guiding modification are circled. The sequences complementary to the active ASOs (462025 and 462026) are marked by lines.

In a separate experiment, the structure of U16 snoRNA was probed. Nuclei were prepared from Hela cells and incubated with or without 3% dimethylsulphate (DMS) at room temperature for 4 min. RNA was prepared and subjected to primer extension using a 5' labeled probe specific to U16 snoRNA. Extension products were analyzed in an 8% polyacrylamide 7M urea gel, next to a DNA sequencing ladder, generated with the same primer. The nucleotides accessible to DMA were identified (FIG. 3). The proposed secondary structure of U16 snoRNA was then generated using the program MFold, and this structure was refined based on the probing data (FIG. 4). The data demonstrates that the U16 snoRNA regions targeted by the two active antisense oligonucleotides exhibit an open structure, suggesting that in this instance, the knockdown efficiency of antisense oligonucleotides correlated with the accessibility of the snoRNA regions.

Example 2: Lack of Inhibition of Human snoRNA U16 in Hela Cells by DNA Oligonucleotide or siRNA Two antisense compounds with the same sequence as ISIS 462026 but with different chemistries were tested for their effect on U16 mRNA in vitro. A DNA oligonucleotide with deoxyribose sugar moieties and phosphorothioate backbone, as well as a double-stranded RNA (siRNA) version of ISIS 462026, were tested in the assays.

Hela cells were cultured on 6-well plates in DMEM medium supplemented with 10% fetal calf serum and 1% penicillin/streptomycin at 37° C. in a 5% $CO_2$ incubator. Sub-confluent cells were treated with either a DNA oligonucleotide or siRNA at concentrations of 10 nM, 30 nM, 40 nM, or 50 nM. The DNA oligonucleotide was transfected in Opti-MEM medium containing 4 μg/mL Lipofectamine 2000 (Invitrogen, CA) for 4 hours, after which the transfection media was replaced with fresh culture medium. The siRNA was transfected using RNAiMax as the transfection agent. After a period of approximately 48 hours, RNA was isolated from the cells and the U16 snoRNA levels were determined by northern hybridization as follows.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U16 snoRNA-specific 5'-end labeled oligonucleotide probe (SEQ ID NO: 2). 5.8S and 5S rRNAs were determined by ethidium bromide staining and served as a control for loading. The density of the bands was scanned using an ImageJ densitometer.

Figure 5:
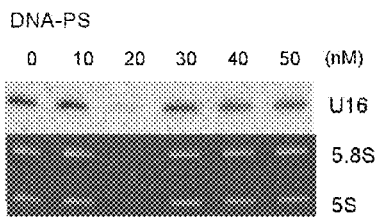
FIG. 5 shows results of an assay with DNA oligonucleotide described in Example 2
Figure 6:
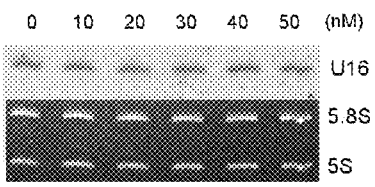
FIG. 6 shows results of an assay with siRNA, described in Example 2

The results for the assay with the DNA oligonucleotide are presented in Table 2 and FIG. 5, as percent inhibition compared to the untreated control. The results from the siRNA experiment are presented in FIG. 6. The assays demonstrate that neither the DNA oligonucleotide nor the siRNA had any significant effect in inhibiting U16 snoRNA. The failure of the siRNA is consistent with a model of activity of ISIS 462026 based on RNase H dependent cleavage in the nucleus or nucleolus, where RISC (necessary for siRNA activity) is absent. The relative failure of the full deoxy DNA antisense oligonucleotide may indicate that compartmentalization and/or structure of snoRNAs requires the additional affinity provided by modifications such as 2'-MOE.

TABLE 2

Percent inhibition of U16 snoRNA by a DNA oligonucleotide compared to the control

| Dose (nM) | % inhibition |
|---|---|
| 10 | 12 |
| 30 | 4 |
| 40 | 34 |
| 50 | 35 |

Example 3: Lack of Inhibition of Human snoRNA U16 in Hela Cells by Uniform 2'MOE/RNA Oligonucleotides Two RNA compounds with the same sequence as ISIS 462025 or ISIS 462026 but with uniform 2'MOE chemistry were tested for their effect on U16 mRNA in vitro.

Hela cells were cultured on 6-well plates in DMEM medium supplemented with 10% fetal calf serum and 1% penicillin/streptomycin at 37° C. in a 5% $CO_2$ incubator. Sub-confluent cells were treated with either 2'MOE/chimeric antisense oligonucleotide or 2'MOE modified phosphorothioate linked RNA oligonucleotide. The sequences of these oligonucleotides were either that of ISIS 462025 or ISIS 462026. The oligonucleotides were transfected in Opti-MEM medium containing 4 μg/mL Lipofectamine 2000 (Invitrogen, CA) for 4 hours, after which the transfection media was replaced with fresh culture medium. After a period of approximately 48 hours, RNA was isolated from the cells and the U16 snoRNA levels were determined by northern hybridization.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U16 snoRNA-specific 5'-end labeled oligonucleotide probe (SEQ ID NO: 2). U80 snoRNA was detected using a specific 5'-end labeled oligonucleotide probe (5'-GATACATCAGA-TAGGAGCGAA-3', designated herein as SEQ ID NO: 26), and served as a loading control. The density of the bands was scanned using an ImageJ densitometer.

Figure 7:
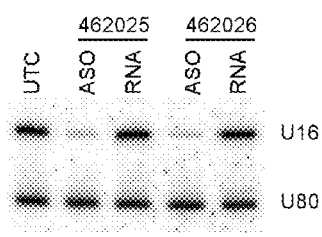
FIG. 7 shows results of an assay with uniform 2'MOE and gapmers described in Example 3

The results are presented in Table 3 and FIG. 7 and demonstrate that the uniform 2'MOE oligonucleotides were not as effective as the chimeric oligonucleotides in inhibiting U16 mRNA. Therefore, this experiment indicates that the inhibition was due to the activity of ISIS 462026 based on RNase H dependent cleavage in the nucleus or nucleolus.

TABLE 3

Percent inhibition of U16 snoRNA compared to the control

|  | % inhibition |
|---|---|
| ASO-462025 | 84 |
| RNA-462025 | 5 |
| ASO-462026 | 85 |
| RNA-462026 | 8 |

Example 4: Time Course of Antisense Inhibition of Human snoRNA U16 in Hela Cells The time course of antisense oligonucleotide-mediated U16 reduction was studied. Hela cells were cultured on 6-well plates in DMEM medium supplemented with 10% fetal calf serum and 1% penicillin/streptomycin at 37° C. in a 5% $CO_2$ incubator. Sub-confluent cells were treated with ISIS 462026 at 50 nM concentration. The oligonucleotides were transfected in Opti-MEM medium containing 4 μg/mL Lipofectamine 2000 (Invitrogen, CA) for 0 hr, 6 hr, 12 hr, 24 hr, 36 hr or 48 hr after which the transfection media was replaced with fresh culture medium. RNA was isolated from the cells and the U16 snoRNA levels were determined by northern hybridization.

Figure 8:
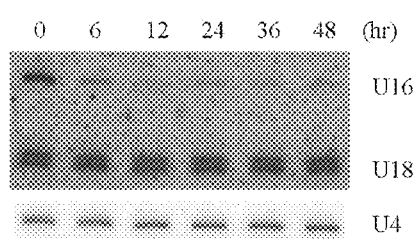
FIG. 8 shows results of a time-dependent assay described in Example 4

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U16 snoRNA-specific 5'-end labeled oligonucleotide probe (SEQ ID NO: 2). U80 snoRNA was detected using a specific 5'-end labeled oligonucleotide probe (SEQ ID NO: 26), and served as a loading control. The density of the bands was scanned using an ImageJ densitometer. The results are presented in Table 4 and FIG. 8. The assays demonstrated that ISIS 462026 inhibited U16 snoRNA expression as early as 6 hours after transfection.

TABLE 4

Time course of inhibition of U16 snoRNA, expressed as percent inhibition compared to the control

| Time (hr) | % inhibition |
|---|---|
| 6 | 82 |
| 12 | 84 |
| 24 | 87 |
| 36 | 91 |
| 48 | 89 |

Example 5: Effect of Various Transfection Reagents on the Antisense Inhibition of Human snoRNA U16 in Hela Cells The effect of using three different transfection reagents, Lipofectamine 2000, RNAiMax, or Oligofectamine, on antisense oligonucleotide-mediated U16 reduction was studied. Hela cells were cultured on 6-well plates in DMEM medium supplemented with 10% fetal calf serum and 1% penicillin/streptomycin at 37° C. in a 5% $CO_2$ incubator. ISIS 462026 was transfected with any one of the transfection reagents (4 μg/mL Lipofectamine 2000, 4 μg/mL Oligofectamine, or 6 μg/mL Lipofectamine RNAiMax) in either of two ways: a) Transfection was performed by adding one of the transfection reagents into the culture medium, followed by addition of ISIS 462026 at 50 nM concentration (designated 'Free'); or b) ISIS 462026 was pre-mixed with one transfection reagent, the resulting mixture was incubated at room temperature for 10 min, and then added to the culture medium (designated 'Pre").

Figure 9:
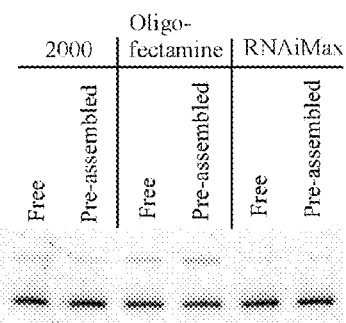
FIGS. 9 and 10 show results of an assay with various transfection reagents described in Example 5
Figure 10:
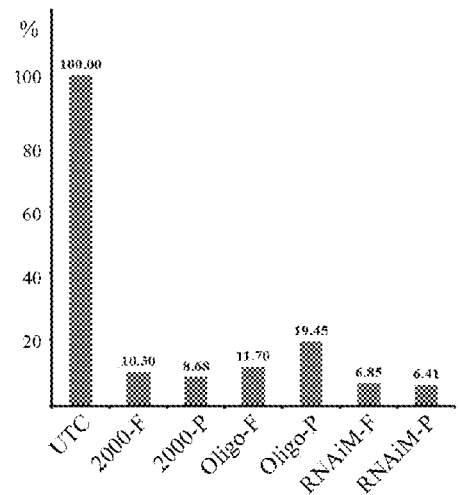

After 4 hours, the medium was replaced with fresh culture medium. RNA was isolated from the cells and the U16 snoRNA levels were determined by northern hybridization. Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U16 snoRNA-specific 5'-end labeled oligonucleotide probe (SEQ ID NO: 2). U80 snoRNA was detected using a specific 5'-end labeled oligonucleotide probe (SEQ ID NO: 26), and served as a loading control. The density of the bands was scanned using an ImageJ densitometer. The results are presented in Table 5, and FIGS. 9 and 10. The assays demonstrate that ISIS 462026 inhibited U16 snoRNA expression irrespective of the transfection reagent or method utilized.

TABLE 5

Antisense inhibition of U16 snoRNA with various transfection reagents and methods of transfection

|  | % inhibition |
|---|---|
| Lipofectamine 2000 (Free) | 90 |
| Lipofectamine 2000 (Pre) | 91 |
| Oligofectamine (Free) | 88 |

TABLE 5-continued

Antisense inhibition of U16 snoRNA with various transfection reagents and methods of transfection

| | % inhibition |
|---|---|
| Oligofectamine (Pre) | 81 |
| RNAiMax (Free) | 93 |
| RNAiMax (Pre) | 94 |

Example 6: Antisense Inhibition of Human U16 snoRNA in Hela, HEK-293 and A549 Cells The effect of treatment of antisense oligonucleotides targeting U16 snoRNA on the human cell lines, HEK-293 and A549, was studied and compared with that in Hela cells. Hela cells, HEK-293 cells and A549 cells were cultured in DMEM medium supplemented with 10% fetal calf serum and 1% penicillin/streptomycin at 37° C. in a 5% $CO_2$ incubator. ISIS 462026 was transfected in each of these cells. After 4 hours, the medium was replaced with fresh culture medium. RNA was isolated from the cells and the U16 snoRNA levels were determined by northern hybridization.

Figure 11:
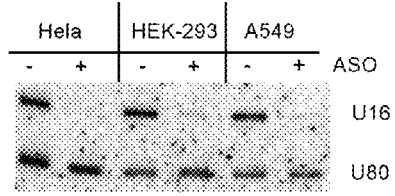
FIG. 11 shows results of an assay using various cell lines described in Example 6

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U16 snoRNA-specific 5'-end labeled oligonucleotide probe (SEQ ID NO: 2). U80 snoRNA was detected using a specific 5'-end labeled oligonucleotide probe (SEQ ID NO: 26), and served as a loading control. The density of the bands was scanned using an ImageJ densitometer. The results are presented in Table 6 and FIG. 11. The assays demonstrate that ISIS 462026 inhibited U16 snoRNA expression with equal potency in each of the cell types used.

TABLE 6

Antisense inhibition of U16 snoRNA in various human cell lines

| Cell type | % inhibition |
|---|---|
| A549 | >95 |
| HEK-293 | 91 |
| Hela | >95 |

Example 7: Effect of Antisense Inhibition of Human snoRNA U16 on the U16 Guide Function The effect of antisense oligonucleotide-mediated U16 reduction on its function in guiding 2'-O-methylation at site A484 of 18S rRNA was studied.

Hela cells were cultured in DMEM medium supplemented with 10% fetal calf serum and 1% penicillin/streptomycin at 37° C. in a 5% $CO_2$ incubator. Sub-confluent cells were treated with ISIS 462025, ISIS 462026, or ISIS 462027 at a 50 nM concentration in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells.

Figure 12:
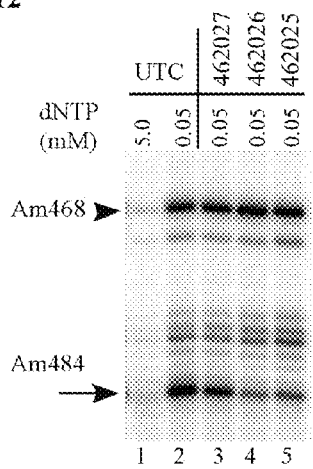
FIG. 12 shows results of a methylation assay described in Example 7. The targeted Am484 is indicated with an arrow and an adjacent modification (Am468) is marked with an arrowhead.

Total RNA was prepared using Tri-Reagent, based on the manufacturer's instructions. Methylation was determined by primer extension assay using two different dNTP concentrations (0.05 and 5 µM), as described in Maden et al (Biochimie. 77: 22-29, 1995). Primer extension products were separated in 8% polyacrylamide-7M urea gels. For quantitative analysis of 2'-O-methylation, RNase H-cleavage assay was performed, as described in Yu et al (RNA. 3: 324-331, 1997). Briefly, 4 µg total RNA was hybridized with 300 pM chimeric oligonucleotide (5'-UmUmdTdGdCdGC-mGmCmCmUmGmCmUmGmCmCmUm-3, designated herein as SEQ ID NO: 27) by heating at 90° C. for 5 min, then 37° C. for 10 min, and cooled on ice for 2 min. Next, 5 µl of 2× RNase H buffer (40 mM Tris.Cl pH 7.5; 20 mM $MgCl_2$; 200 mM KCl; 50 mM DTT; 10% sucrose) containing 3 units of RNase H (New England Biolabs, MA) and 2 units of RNase Inhibitor (New England Biolabs, MA) were added. The RNA was digested at 37° C. for 60 min, and separated in a 1.2% agarose gel. 18S rRNA and its 5' cleaved products were detected by northern hybridization using a 5' end-labeled probe (5'-GCTACTGGCAGGATCAACCA-3', designated herein as SEQ ID NO: 28). The methylation level of A484 was strongly decreased in cells treated with ISIS 462025 or ISIS 462026 (FIG. 12). Treatment with ISIS 462027 resulted in partial reduction in methylation of A484. Methylation of a neighboring site (A468) not mediated by U16 activity was unchanged.

Figure 13:
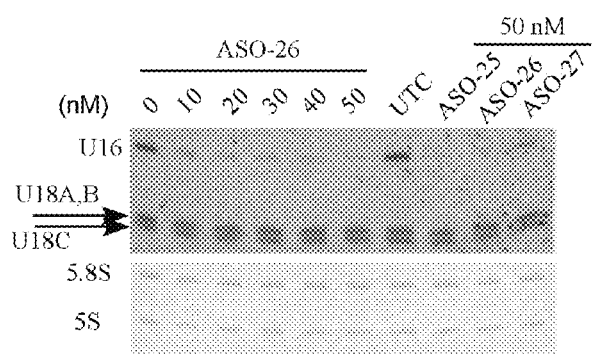
FIG. 13 shows results of an assay on Hela cells described in Example 7.

Separately, Hela cells were treated for 48 hr with 10 nM, 20 nM, 30 nM, 40 nM, or 50 nM of ISIS 462026, or with 50 nM of ISIS 462025 or ISIS 462027. Total RNA was prepared and subjected to northern hybridization as described above. Probes specific to U16 (SEQ ID NO: 2) and U18 (5'-TGTTTCAGAAACACGGACC-3', designated herein as SEQ ID NO: 29) snoRNAs were used to detect the respective RNAs. 5.8S and 5S rRNAs were detected by ethidium bromide staining and served as loading controls. The results demonstrate that these antisense oligonucleotides, which significantly inhibited U16 (Table 7 and FIG. 13) did not affect the level of U18 snoRNAs, which is encoded in the same pre-mRNA.

TABLE 7

Antisense inhibition of U16 snoRNA

| ISIS No. | Dose (nM) | % inhibition |
|---|---|---|
| 462026 | 10 | 68 |
| | 20 | 83 |
| | 30 | 86 |
| | 40 | 88 |
| | 50 | 91 |
| 462025 | 50 | 91 |
| 462027 | 50 | 56 |

Figure 14:
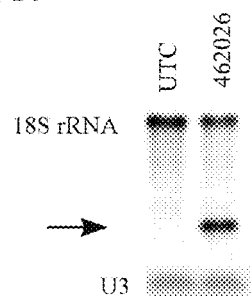
FIG. 14 shows results of A484 methylation assay described in Example 7.

Reduction of A484 methylation was confirmed using an oligonucleotide directed, site-specific RNaseH cleavage assay, in which only the 18S rRNA lacking A484 methylation could be cleaved. In that assay, approximately 55% of 18S rRNA from U16 depleted cells was cleaved, whereas no cleavage was found for control rRNA (FIG. 14). These results indicate that antisense-mediated depletion of U16 snoRNA specifically inactivated the methylation guided by this snoRNA, and that the predicted function of this RNA could be confirmed.

Example 8: Effect of Antisense Inhibition of Human snoRNA U16 on its Host mRNA, RPL4

Figure 15:
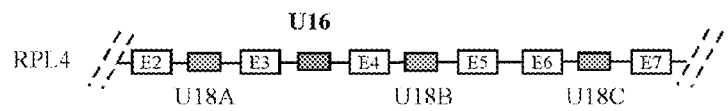
FIG. 15 provides a schematic depiction of the U16 snoRNA gene locus discussed in Example 8. The partial host pre-mRNA (RPL4) is shown. The gray boxes indicate intronic snoRNAs (U16 and three isoforms of U18 snoRNA) in the host gene. E2-E7, exons of RPL4 pre-mRNA.

U16 snoRNA is embedded in an intron of its host gene, RPL4, as shown in FIG. 15 (Lestrade, L. and Weber, M. J.

Nucleic Acid Res. 34: D158-162, 2006). The effect of antisense oligonucleotide-mediated U16 reduction on the pre-mRNA levels was studied.

Hela cells were cultured in DMEM medium supplemented with 10% fetal calf serum and 1% penicillin/streptomycin at 37° C. in a 5% $CO_2$ incubator. Sub-confluent cells were treated with ISIS 462025, ISIS 462026, or ISIS 462027 at a 50 nM concentration in Opti-MEM medium containing 4 μg/mL Lipofectamine 2000 (Invitrogen, CA) for 4 hours, after which the transfection was replaced with fresh culture medium. After a period of approximately 48 hours, RNA was isolated from the cells and the U16 snoRNA levels were determined by northern hybridization.

Figure 16:
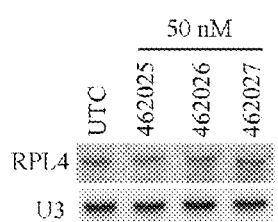
FIG. 16 shows results of the northern hybridization assay described in Example 8.

Total RNA was prepared using Tri-Reagent, based on the manufacturer's instructions. Five micrograms of total RNA was separated in 6% polyacrylamide-7M urea gels and was transferred onto a membrane, using semi-dry transfer apparatus. Northern hybridization was performed using a RPL4-specific 5'-end labeled oligonucleotide probe (5'-CAGGGCAGAACAGATGGCGTATC-3', designated herein as SEQ ID NO: 30). U3 snoRNA was detected using a specific 5'-end labeled oligonucleotide probe (5'-ACCACTCAGAC-CGCGTTCTCTCC-3', designated herein as SEQ ID NO: 31), and served as a loading control. The density of the bands was scanned using an ImageJ densitometer. The results are presented in FIG. 16 and demonstrate that the level of mature RPL4 mRNA was not altered by treatment with antisense oligonucleotides targeting U16.

Figure 17:
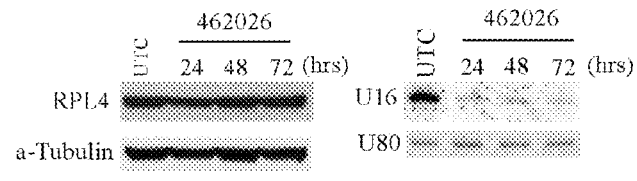
FIG. 17 shows Western blot analysis of an assay described in Example 8.

Separately, Hela cells were treated with ISIS 462026 for 24, 48 or 72 hr and harvested and lysed. Whole cell lysates were separated in 4-12% gradient SDS-PAGE gels. Proteins were transferred to PVDF membrane for 1 hour using a semi-dry transfer apparatus at 25 volt constant. The membranes were blocked for 1 hr with block buffer (5% dry milk in 1×TBS), and incubated with primary antibodies against RPL4 (11302-1-AP, Proteintech, 1:1500) or alpha tubulin (T-5168, Sigma, 1:8000) at room temperature for 3-4 hours. After 3 washes with wash buffer (1×TBS, 0.1% Tween-20), membranes were incubated with anti-rabbit or anti-mouse secondary antibody at room temperature for 1 hr. After 3 washes, proteins were detected using ECL (Abcam). The results are presented in FIG. 17 and demonstrate that there was no change in levels of RPL4 protein even after 3 days of antisense oligonucleotide treatment.

Thus, these oligonucleotides inhibited mature U16 snoRNA, but not other messages from the same pre-mRNA, suggesting that they may act on the mature snoRNA after splicing.

Figure 18:
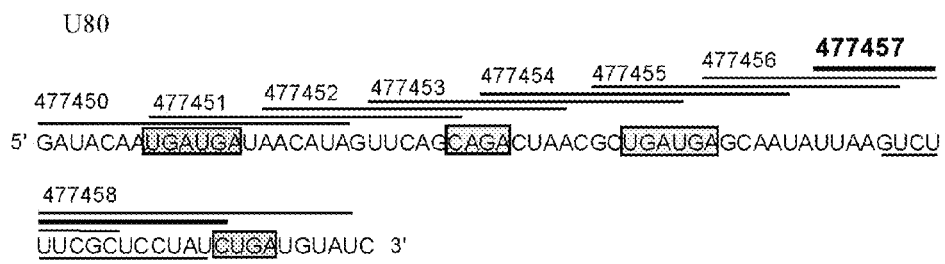
FIG. 18 shows the sequence of U80 snoRNA, as described in Example 9. The C and D motifs are boxed, and the sequence involved in guiding rRNA modification is underlined. The targeted positions of ASOs are indicated. The active ASO is marked by a thick line.
Figure 19:
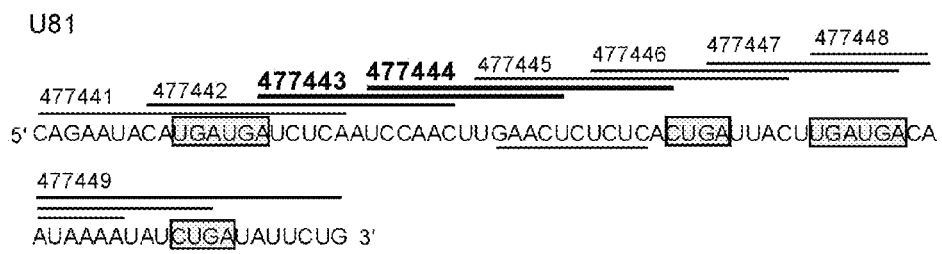
FIG. 19 shows the sequence of U81 snoRNA, described in Example 9.
Figure 20:
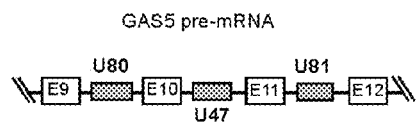
FIG. 20 shows gene organization of U80 and U81 snoRNAs in the introns of GAS5 gene, as described in Example 9. A partial map of the precursor is shown. Gray boxes indicate the intronic snoRNAs. The E9-E12 exons of GAS5 gene are shown in open boxes.

Example 9: Antisense Inhibition of Human C/D Box snoRNAs U80 and U81 in Hela Cells Antisense oligonucleotides targeting a U80 and U81 snoRNA nucleic acids were designed (FIGS. 18 and 19). U80 and U81 are C/D box RNAs that are encoded in different introns of the same host non-protein-coding RNA, GAS5 (Smith, C. M. and Steitz, J. A. Mol. Cell. Biol. 18: 6897-6909, 1998), as shown in FIG. 20. The oligonucleotides were tested for their effects on U80 and U81 mRNA in vitro.

Hela cells were cultured on 6-well plates in DMEM medium supplemented with 10% fetal calf serum and 1% penicillin/streptomycin at 37° C. in a 5% $CO_2$ incubator. Sub-confluent cells were treated with the antisense oligonucleotides at a 50 nM concentration in Opti-MEM medium containing 4 μg/mL Lipofectamine 2000 (Invitrogen, CA) for 4 hours, after which the transfection was replaced with fresh culture medium. After a period of approximately 48 hours, RNA was isolated from the cells and the U80 or U81 snoRNA levels were determined by northern hybridization.

Figure 21:
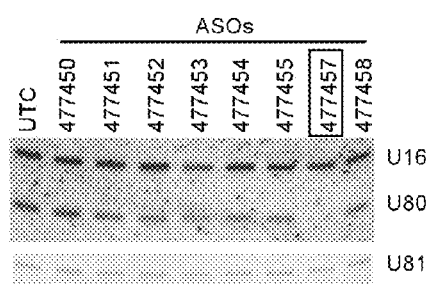
FIG. 21 shows results of an assay with Hela cells described in Example 9.
Figure 22:
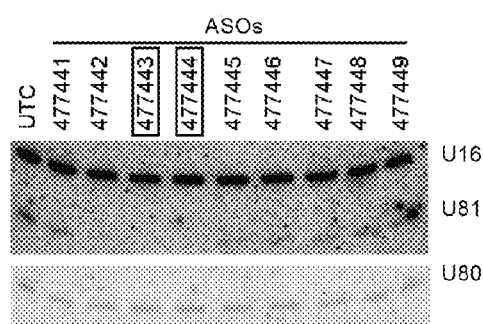
FIG. 22 shows results of an assay with Hela cells probed for U81 snoRNA described in Example 9.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U80 snoRNA-specific 5'-end labeled oligonucleotide probe (SEQ ID NO: 26) or U81 snoRNA-specific 5'-end labeled oligonucleotide probe (5'-CAGAATATCAGATATTTTATTG-3', designated herein as SEQ ID NO: 32). The U16 snoRNA-specific probe (SEQ ID NO: 2) served as a control for loading. The density of the bands was scanned using an ImageJ densitometer. Results for inhibition of U80 snoRNA are presented in Table 8 and in FIG. 21. The data indicate that ISIS 477457 significantly inhibited U80 snoRNA expression. Results for inhibition of U81 snoRNA are presented in FIG. 22. The data indicate that ISIS 477443 and ISIS 477444 significantly inhibited U81 snoRNA expression.

The chimeric antisense oligonucleotides in Tables 8 and 9 were designed as 5-10-5 MOE gapmers with phosphorothioate (P=S) linkages throughout. All cytidine residues throughout each gapmer are 5-methylcytidines. Each gapmer listed in Table 8 is targeted to SEQ ID NO: 33 (complement of GENBANK Accession No. NT_004487.19 truncated from nucleotides 25322609 to 25322686). Each gapmer listed in Table 9 is targeted to SEQ ID NO: 34 (complement of GENBANK Accession No. NT_004487.19 truncated from nucleotides 25321926 to 25322002).

TABLE 8

Antisense inhibition by chimeric antisense oligonucleotides having 5-10-5 MOE wings and deoxy gap targeted to U80 snoRNA

| Start Site | Stop Site | ISIS No. | Sequence | % inhibition | SEQ ID NO. |
|---|---|---|---|---|---|
| 1 | 20 | 477450 | TATGTTATCATCATTGTATC | 11 | 35 |
| 8 | 27 | 477451 | GCTGAACTATGTTATCATCA | 42 | 36 |
| 15 | 34 | 477452 | TTAGTCTGCTGAACTATGTT | 56 | 37 |
| 22 | 41 | 477453 | ATCAGCGTTAGTCTGCTGAA | 25 | 38 |
| 29 | 48 | 477454 | ATTGCTCATCAGCGTTAGTC | 42 | 39 |
| 36 | 55 | 477455 | ACTTAATATTGCTCATCAGC | 50 | 40 |

TABLE 8-continued

Antisense inhibition by chimeric antisense oligonucleotides having 5-10-5 MOE wings and deoxy gap targeted to U80 snoRNA

| Start Site | Stop Site | ISIS No. | Sequence | % inhibition | SEQ ID NO. |
|---|---|---|---|---|---|
| 50 | 69 | 477457 | GATAGGAGCGAAAGACTTAA | 96 | 41 |
| 58 | 77 | 477458 | ATACATCAGATAGGAGCGAA | 56 | 42 |

TABLE 9

Chimeric antisense oligonucleotides having 5-10-5 MOE wings and deoxy gap targeted to U81 snoRNA

| Start Site | Stop Site | ISIS No. | Sequence | SEQ ID NO. |
|---|---|---|---|---|
| 1 | 20 | 477441 | TGAGATCATCATGTATTCTG | 43 |
| 8 | 27 | 477442 | GTTGGATTGAGATCATCATG | 44 |
| 15 | 34 | 477443 | AGTTCAAGTTGGATTGAGAT | 45 |
| 22 | 41 | 477444 | GTGAGAGAGTTCAAGTTGGA | 46 |
| 29 | 48 | 477445 | GTAATCAGTGAGAGAGTTCA | 47 |
| 36 | 55 | 477446 | TCATCAAGTAATCAGTGAGA | 48 |
| 43 | 62 | 477447 | TTTATTGTCATCAAGTAATC | 49 |
| 50 | 69 | 477448 | CAGATATTTTATTGTCATCA | 50 |
| 58 | 77 | 477449 | CAGAATATCAGATATTTTAT | 51 |

Figure 23:
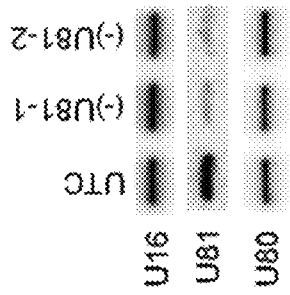
FIG. 23 shows Northern hybridization for U80 snoRNA in Hela cells, as described in Example 9.
Figure 24:
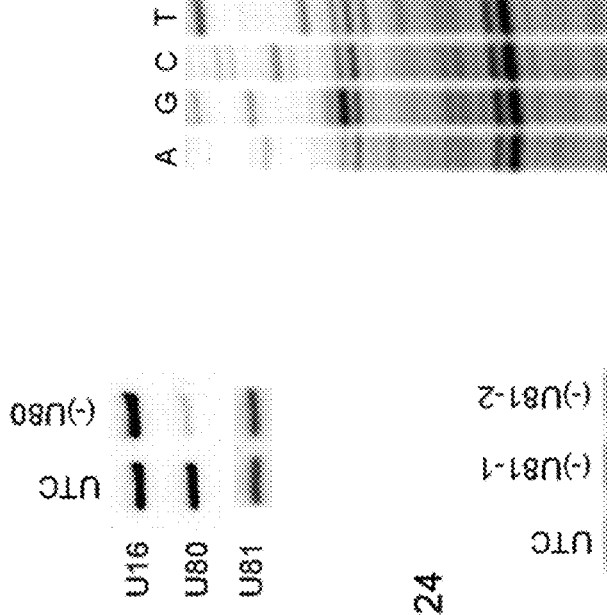
FIG. 24 shows results of an assay for U81 snoRNA by U81-specific ASOs described in Example 9.

Separately, Hela cells were treated with 50 nM concentration of ISIS 477457, ISIS 477443, or ISIS 477444. Total RNA was prepared and subjected to northern hybridization, as described earlier. The results are presented in Table 10 and FIGS. 23 and 24. The data demonstrate significant reductions of the specific snoRNAs by the antisense oligonucleotides. FIGS. 23 and 24 also demonstrate that knockdown occurs at the mature snoRNA level as depletion of U80 by its specific antisense oligonucleotide does not affect the levels of U81 snoRNA, and vice versa.

TABLE 10

Antisense inhibition by chimeric antisense oligonucleotides of U80 and U81 snoRNAs

| ISIS No | Target | % inhibition |
|---|---|---|
| 477457 | U80 | 87 |
| 477443 | U81 | 85 |
| 477444 | | 82 |

Example 10: Effect of Antisense Inhibition of Human snoRNAs U80 and U81 on their Guide Function The effect of antisense oligonucleotide-mediated U80 reduction on its function in guiding 2'-O-methylation at site G1612 of 28S rRNA, as well as the effect of antisense oligonucleotide-mediated U81 reduction on its function in guiding 2'-O-methylation at site A391 of 28S rRNA, was studied.

Hela cells were cultured in DMEM medium supplemented with 10% fetal calf serum and 1% penicillin/streptomycin at 37° C. in a 5% $CO_2$ incubator. Sub-confluent cells were treated with ISIS 477457 or ISIS 477443 at a 50 nM concentration in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells.

Figure 26:
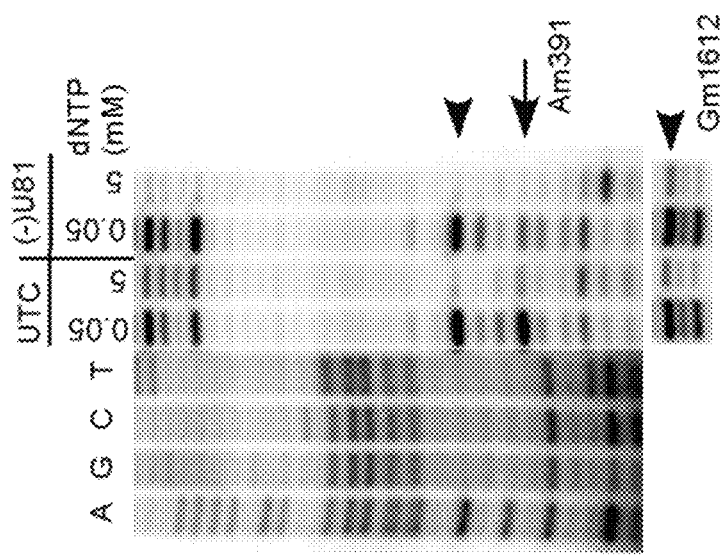
FIG. 26 shows results of a depletion assay of U81 snoRNA and its effect on its function in guiding methylation at site A391 of 28S rRNA, as described in Example 10.
Figure 25:
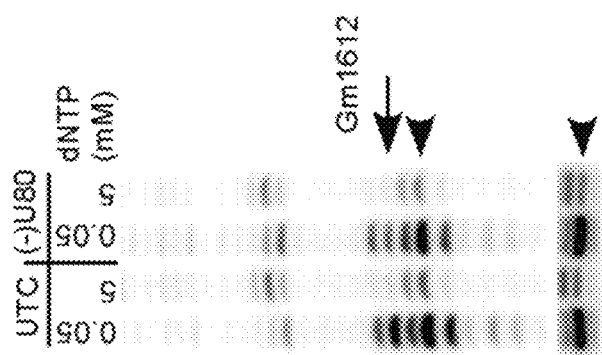
FIG. 25 shows results of a depletion assay of U80 snoRNA and effect on the level of methylation at the predicted site in 28S rRNA (G1612) described in Example 10. A neighboring methylation site is marked with an arrowhead. The methylation level of A391 guided by U81 snoRNA was not affected by depletion of U80 snoRNA, as determined by primer extension using a different primer (lower panel).

Total RNA was prepared using Tri-Reagent, based on the manufacturer's instructions. Methylation was determined by primer extension assay using two different dNTP concentrations (0.05 and 5 µM), as described earlier. The methylation level of G1612 was strongly decreased in cells treated with ISIS 477457 (FIG. 25) and the methylation of A391 was strongly decreased in cells treated with ISIS 477443 (FIG. 26). The methylation level of G1612 guided by U80 was not affected by U81 snoRNA depletion. Similarly, the methylation level of A391 guided by U81 was not affected by U80 snoRNA depletion.

Example 11: Antisense Inhibition of Isoforms of a Human C/D Box snoRNA, U50 and U50B in Hela Cells Antisense oligonucleotides were designed targeting the isoforms of a human C/D box snoRNA, U50 and U50B, which are encoded in different introns of the same host gene (SNHG5) (Tanaka, et al., Genes Cells. 5: 277-287, 2000), and share approximately 80% identity (FIGS. 27 and 28). The gapmers were tested for their effects on U50 and U50B mRNA in vitro.

Hela cells were cultured on 6-well plates in DMEM medium supplemented with 10% fetal calf serum and 1% penicillin/streptomycin at 37° C. in a 5% $CO_2$ incubator. Sub-confluent cells were treated with the antisense oligonucleotides at a 50 nM concentration in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells and U50 snoRNA levels were determined by northern hybridization.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U50 snoRNA-specific 5'-end labeled oligonucleotide probe (5'-GGTTCGGGATAAGATCATCACA-3', designated herein as SEQ ID NO: 52) and a U50B snoRNA-specific 5'-end labeled oligonucleotide probe (5'-CGTACTTATTTTTCT-TCAGGTTA-3', designated herein as SEQ ID NO: 53). The U16 snoRNA-specific probe (SEQ ID NO: 53) served as a control for loading. The density of the bands was scanned using an ImageJ densitometer. Results for inhibition of U50 snoRNA are presented in Table 11 and FIG. 29. The data indicates that ISIS 477498 and ISIS 477499 significantly inhibited U50 snoRNA expression, but did not affect U50B expression (FIG. 29). ISIS 477499 has only 3 mismatches with the U50B snoRNA sequence (FIG. 30) but failed to inhibit U50B levels.

The chimeric antisense oligonucleotides in Table 11, and also described in FIG. 31, were designed as 5-10-5 MOE gapmers. The gapmers are 20 nucleotides in length, wherein the central gap segment is comprised of ten 2'-deoxynucleotides and is flanked on both sides (in the 5' and 3' directions) by wings comprising five nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. Each gapmer listed in Table 11 is targeted to SEQ ID NO: 54 (the complement of GENBANK Accession No. NT_007299.13 truncated from nucleotides 24505000 to 24510000).

Example 12: Effect of Antisense Inhibition of Human snoRNAs U50 and U50B on their Guide Function The effect of antisense oligonucleotide-mediated U50 reduction on its function in guiding 2'-O-methylation at site C2848 of 28S rRNA was studied.

Hela cells were cultured in DMEM medium supplemented with 10% fetal calf serum and 1% penicillin/streptomycin at 37° C. in a 5% $CO_2$ incubator. Sub-confluent cells were treated with ISIS 477499 or ISIS 485259 at 50 nM concentration in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells.

Total RNA was prepared using Tri-Reagent, based on the manufacturer's instructions. Methylation was determined by

TABLE 11

Antisense inhibition by chimeric antisense oligonucleotides having 5-10-5 MOE wings and deoxy gap targeted to U50 snoRNA

| Start Site | Stop Site | ISIS No. | Sequence | % inhibition | SEQ ID NO. |
|---|---|---|---|---|---|
| 3081 | 3100 | 477493 | GGATAAGATCATCACAGATA | 45 | 55 |
| 3086 | 3105 | 477494 | GTTCGGGATAAGATCATCAC | 62 | 56 |
| 3091 | 3110 | 477495 | TTCAGGTTCGGGATAAGATC | 79 | 57 |
| 3096 | 3115 | 477496 | AGAAGTTCAGGTTCGGGATA | 79 | 58 |
| 3101 | 3120 | 477497 | TCAACAGAAGTTCAGGTTCG | 91 | 59 |
| 3129 | 3148 | 477498 | AAGCCAGATCCGTAAAAGTT | 97 | 60 |
| 3134 | 3153 | 477499 | CTCAGAAGCCAGATCCGTAA | 98 | 61 |

In a separate experiment, Hela cells were treated for 48 hr with 50 nM of ISIS 477499, targeting U58 snoRNA or 50 nM of ISIS 485259 (CTCAGAAGCCGAATCCGTAG, mismatched by 3 nucleobases to SEQ ID NO: 62), targeting the U50B isoform, or 30 nM of both antisense oligonucleotides together. Total RNA was prepared and subjected to northern hybridization using 5'-end labeled oligonucleotides specific to U50 or U50B. U6 snRNA (5'-TGGAACGCTTCAC-GAATTTGCG-3', designated herein as SEQ ID NO: 63) was detected and served as a loading control. The results are presented in Table 12 and FIG. 32 and demonstrate that the antisense oligonucleotides target their specific isoforms only.

TABLE 12

Antisense inhibition by chimeric antisense oligonucleotides targeted to U50 and U50B snoRNA

| ISIS No. | % inhibition | |
|---|---|---|
| | U50 | U50B |
| 477499 | 91 | 11 |
| 485259 | 7 | 74 |
| 477499 + 485459 | 93 | 84 | primer extension assay using two different dNTP concentrations (0.05 and 5 µM), as described earlier. The results are presented in FIG. 33 and demonstrate that the inhibition of U50 or U50B snoRNA impairs the methylation guided by this RNA. Co-depletion of the two snoRNAs, as shown in the Figure, caused greater reduction in methylation, indicating that both isoforms are functional. This data also indicates that more than one snoRNA can be reduced simultaneously.

Example 13: Antisense Inhibition of Isoforms of a Human H/ACA Box snoRNA, U23 in Hela Cells Antisense oligonucleotides were designed targeting the human H (AnAnnA) and ACA box intronic snoRNA, U23 (FIGS. 34 and 35) (Lestrade, L. and Weber, M. J. Nucleic Acids Res. 34: D158-162, 2006). The gapmers were tested for their effects on U23 mRNA in vitro.

Hela cells were cultured on 6-well plates in DMEM medium supplemented with 10% fetal calf serum and 1% penicillin/streptomycin at 37° C. in a 5% $CO_2$ incubator. Sub-confluent cells were treated with the antisense oligonucleotides at a 50 nM concentration in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells and U23 snoRNA levels were determined by northern hybridization.

Figure 36:
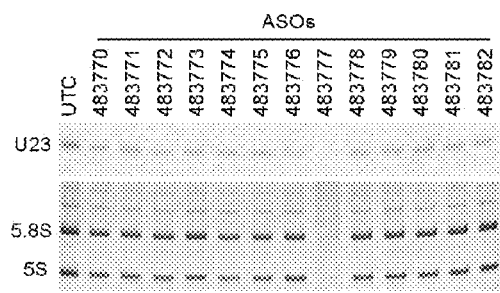
FIG. 36 shows results from a Northern hybridization of U23 snoRNA, as described in Example 13.
Figure 36:
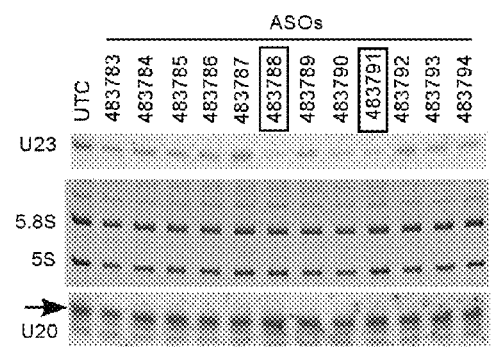
Figure 37:
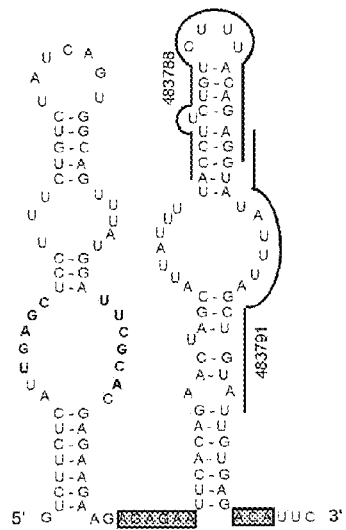
FIG. 37 shows the positions of two active ASOs in the secondary structure of U23 snoRNA. indicated by lines. The snoRNA structure was predicted using program MFold. The snoRNA sequences involved in guiding modification are shown in bold.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using a U23 snoRNA-specific 5'-end labeled oligonucleotide probe (5'-GAATGTCTCACAATACAGCTAAAT-3', designated herein as SEQ ID NO: 64). 5.8S and 5S rRNAs were detected by ethidium bromide staining and served as a control for loading. The density of the bands was scanned using an ImageJ densitometer. Results for inhibition of U23 snoRNA are presented in Table 13 and FIG. 36. The data indicates that ISIS 483788 and ISIS 483791 significantly inhibited U23 snoRNA expression. The positions of these two antisense oligonucleotides in the secondary structure of U23 snoRNA is indicated by lines in FIG. 37. The snoRNA structure was predicted using the program MFold and the snoRNA sequences involved in guiding modification is shown in bold in this Figure.

The blot was also probed for U20 snoRNA, which occurs in the same pre-mRNA as U23 (FIG. 34), using a U20-specific 5'-end labeled oligonucleotide probe (5'-CTGGATCAGAACTTGACTATC-3', designated herein as SEQ ID NO: 65). The data is presented in FIG. 36 (lower panel) and demonstrates that antisense inhibition of U23 snoRNA did not affect U20 snoRNA levels, and therefore, that inhibition of U23 was specific and occurred at the mature U23 mRNA level.

The chimeric antisense oligonucleotides in Table 13 were designed as 5-10-5 MOE gapmers. The gapmers are 20 nucleotides in length, wherein the central gap segment is comprised of ten 2'-deoxynucleotides and is flanked on both sides (in the 5' and 3' directions) by wings comprising five nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. Each gapmer listed in Table 13 is targeted to SEQ ID NO: 66 (GENBANK Accession No. NR_002921.1).

TABLE 13

Antisense inhibition by chimeric antisense oligonucleotides having 5-10-5 MOE wings and deoxy gap targeted to U23 snoRNA

| Start Site | Stop Site | ISIS No. | Sequence | % inhibition | SEQ ID NO. |
|---|---|---|---|---|---|
| 1 | 20 | 483770 | AAGGAGCTCAATGAGAAGAC | 0 | 67 |
| 6 | 25 | 483771 | ACAGAAAGGAGCTCAATGAG | 0 | 68 |
| 11 | 30 | 483772 | GATAGACAGAAAGGAGCTCA | 0 | 69 |
| 16 | 35 | 483773 | CCACTGATAGACAGAAAGGA | 0 | 70 |
| 21 | 40 | 483774 | AACTGCCACTGATAGACAGA | 0 | 71 |
| 26 | 45 | 483775 | CCATAAACTGCCACTGATAG | 0 | 72 |
| 31 | 50 | 483776 | CGAATCCATAAACTGCCACT | 0 | 73 |
| 36 | 55 | 483777 | TCGTGCGAATCCATAAACTG | 0 | 74 |
| 41 | 60 | 483778 | TCTTCTCGTGCGAATCCATA | 0 | 75 |
| 46 | 65 | 483779 | TCTCTTCTTCTCGTGCGAAT | 0 | 76 |
| 51 | 70 | 483780 | AATTCTCTCTTCTTCTCGTG | 0 | 77 |
| 56 | 75 | 483781 | CTGTGAATTCTCTCTTCTTC | 0 | 78 |
| 61 | 80 | 483782 | TAGTTCTGTGAATTCTCTCT | 0 | 79 |
| 71 | 90 | 483784 | AAAATAATGCTAGTTCTGTG | 0 | 80 |
| 76 | 95 | 483785 | AAGGTAAAATAATGCTAGTT | 0 | 81 |
| 81 | 100 | 483786 | GACAGAAGGTAAAATAATGC | 0 | 82 |
| 86 | 105 | 483787 | GTAAAGACAGAAGGTAAAAT | 0 | 83 |
| 91 | 110 | 483788 | CCTCTGTAAAGACAGAAGGT | 82 | 84 |
| 96 | 115 | 483789 | ATATACCTCTGTAAAGACAG | 0 | 85 |
| 101 | 120 | 483790 | GCTAAATATACCTCTGTAAA | 0 | 86 |
| 106 | 125 | 483791 | ATACAGCTAAATATACCTCT | 69 | 87 |
| 111 | 130 | 483792 | TCACAATACAGCTAAATATA | 0 | 88 |
| 116 | 135 | 483793 | ATGTCTCACAATACAGCTAA | 0 | 89 |
| 118 | 137 | 483794 | GAATGTCTCACAATACAGCT | 0 | 90 |

Figure 38:
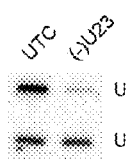
FIG. 38 shows results from a Northern hybridization for U23 snoRNA in cells treated [(–)U23] or not treated (UTC) with 50 nM of a lead ASO targeting this snoRNA (ASO483788). U16 snoRNA was detected and served as a loading control.

In a separate experiment, Hela cells were treated for 48 hr with 50 nM of ISIS 483788. Total RNA was prepared and subjected to northern hybridization using 5'-end labeled oligonucleotides specific to U23 or U50B. U16 snoRNA (SEQ ID NO: 2) was detected and served as a loading control. The results are presented in FIG. 38 and demonstrate that U23 snoRNA was significantly inhibited by 86%.

Figure 34:
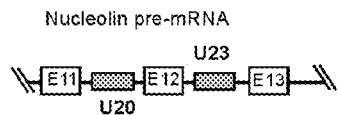
FIG. 34 provides a schematic representation of partial pre-mRNA of Nucleolin gene. The intronic snoRNAs U23 (H/ACA type) and U20 (C/D type) are shown in gray boxes.
Figure 35:
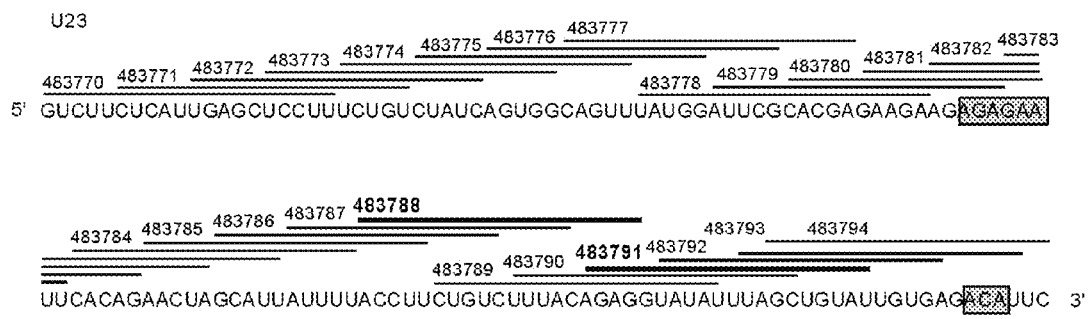
FIG. 35 shows positions of ASOs in U23 snoRNA. The H (AnAnnA) and ACA motifs are shown in gray boxes. The active ASOs identified in panel b are indicated by thick lines and the names are in bold.

Example 14: Effect of Antisense Inhibition of Human snoRNA U23 on its Host Nucleolin Protein Level U16 snoRNA is embedded in an intron of its host gene, Nucleolin, as shown in FIG. 34. The effect of antisense oligonucleotide-mediated U23 reduction on Nucleolin protein levels was studied.

Figure 39:
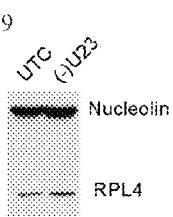
FIG. 39 shows that the protein level of Nucleolin was not affected by the U23 ASO, as determined by western analysis. RPL4 protein was also probed and served as a loading control.

Hela cells were cultured in DMEM medium supplemented with 10% fetal calf serum and 1% penicillin/streptomycin at 37° C. in a 5% $CO_2$ incubator. Sub-confluent cells were treated with ISIS 483788 at a 50 nM concentration in Opti-MEM medium containing 4 µg/mL Lipofectamine 2000 (Invitrogen, CA) for 4 hours, after which the transfection was replaced with fresh culture medium. After a period of approximately 48 hours, cells were harvested and lysed. Whole cell lysates were separated in 4-12% gradient SDS-PAGE gels. Proteins were transferred to PVDF membrane for 1 hour using a semi-dry transfer apparatus at 25 volt constant. The membranes were blocked for 1 hr with block buffer (5% dry milk in 1×TBS), and incubated with primary antibodies against RPL4 (11302-1-AP, Proteintech, 1:1500) or nucleolin at room temperature for 3-4 hours. After 3 washes with wash buffer (1×TBS, 0.1% Tween-20), membranes were incubated with anti-rabbit or anti-mouse secondary antibody at room temperature for 1 hr. After 3 washes, proteins were detected using ECL (Abcam). The results are presented in FIG. 39 and demonstrate that there was no change in levels of Nucleolin protein. The RPL4 protein was also probed and served as a loading control.

Therefore, these observations indicate that ISIS 483788 specifically acts on mature U23 snoRNA.

Example 15: Effect of Antisense Inhibition of Human snoRNA U23 on its Guide Function The effect of antisense oligonucleotide-mediated U23 reduction on its function in guiding the pseudouridylation at site U93 of 18S rRNA (Lestrade, L. and Weber, M. J. Nucleic Acids Res. 34: D158-162, 2006) was studied.

Hela cells were cultured in DMEM medium supplemented with 10% fetal calf serum and 1% penicillin/streptomycin at 37° C. in a 5% $CO_2$ incubator. Sub-confluent cells were treated with ISIS 483788 at 50 nM concentration in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells.

Figure 40:
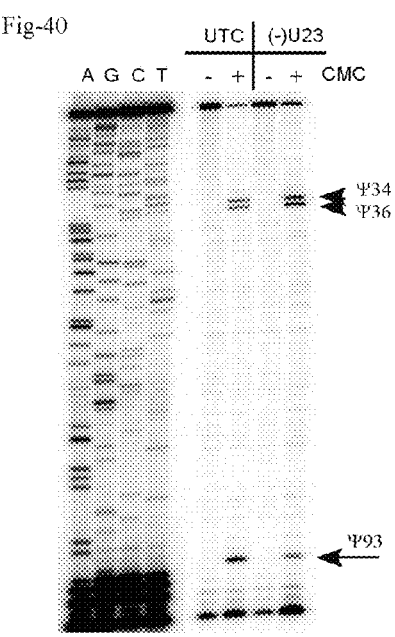
FIG. 40 shows depletion of U23 H/ACA snoRNA impaired its function in guiding pseudouridylation at site U93 of 18S rRNA. Total RNA from test cells was treated with N-cyclohexyl-N'-(2-morpholinoethyl)-carbodiimide methyl-p-toluolsulfonate (CMC), and subjected to primer extension analysis using a 5' end-labeled primer specific to U93 region of 18S rRNA. CMC treatment causes extension to stop one nucleotide before the pseudouridine sites. Extension products were separated in an 8% polyacrylamide gel, next to primer extension sequencing reactions preformed with the same primer. The targeted pseudouridylation site (Ψ93) is indicated. Two other pseudouridines (Ψ34 and Ψ36) in 18S rRNA are marked with arrowheads.

Total RNA from test cells was treated with N-cyclohexyl-N'-(2-morpholinoethyl)-carbodiimide methyl-p-toluolsulfonate (CMC), and subjected to primer extension analysis using a 5' end-labeled primer specific to U93 region of 18S rRNA (5'-AAGGAACCATAACTGATTTAAT-3', designated herein as SEQ ID NO: 91). CMC treatment causes extension to stop one nucleotide before the pseudouridine sites. Extension products were separated in an 8% polyacrylamide gel, next to primer extension sequencing reactions preformed with the same primer. The targeted pseudouridylation site (Ψ93) is indicated in FIG. 40. Two other pseudouridines (Ψ34 and Ψ36) in 18S rRNA are marked with arrowheads and serve as loading controls.

The data in the figure indicates that depletion of U23 also disrupted its guide function, as evidenced by the significantly reduced level of pseudouridylation at position U93 of 18S rRNA. Thus, H/ACA RNAs can also be depleted by 2'MOE/chimeric antisense oligonucleotides.

Example 16: Simultaneous Antisense Inhibition of snoRNAs U16, U50, U80, U81 and U23 in Hela Cells Antisense oligonucleotides targeting snoRNAs U16, U50, U80, U81 and U23 were tested in vitro to study the effect of simultaneous dosing.

Hela cells were cultured on 6-well plates in DMEM medium supplemented with 10% fetal calf serum and 1% penicillin/streptomycin at 37° C. in a 5% $CO_2$ incubator. Sub-confluent cells were co-transfected with 10 nM of ISIS 462026, ISIS 477499, ISIS 477457 and ISIS 477443, as well as 20 nM of ISIS 483788, in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells and the respective snoRNA levels were determined by northern hybridization.

Figure 41:
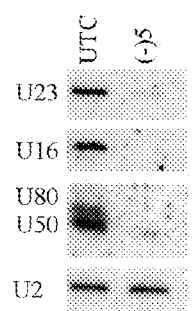
FIG. 41 shows a co-depletion assay described in Example 16.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using the respective snoRNA-specific 5'-end labeled oligonucleotide probes. The U2 snRNA-specific probe served as a control for loading. The density of the bands was scanned using an ImageJ densitometer. Results for inhibition of the respective snoRNA are presented in Table 14 and FIG. 41. The data indicates that multiple snoRNAs can be co-depleted. Hence, antisense oligonucleotide may be utilized in studies on the effects of snoRNAs in a functional domain of the ribosome (for example, Liang X. H. et al., Mol. Cell. 28: 965-977, 2007), where several snoRNAs require to be depleted.

TABLE 14

Simultaneous antisense inhibition by chimeric antisense oligonucleotides

| | % inhibition |
|---|---|
| U23 | 85 |
| U81 | 90 |
| U16 | >95 |
| U50 | >95 |
| U80 | >95 |

Example 17: Antisense Inhibition of scaRNA ACA45 in Hela Cells

Figure 42:
FIG. 42 shows targeted positions of ASOs in ACA45 snoRNA. The H and ACA motifs are boxed. The active ASOs are indicated with thick lines and named with bold letters.

Antisense oligonucleotides were designed targeting RNAs present in Cajal bodies (scaRNAs) that guide modification in snRNAs (Darzacq, X. et al., EMBO J. 21: 2746-2756, 2002). Specifically, antisense oligonucleotides were designed to target scaRNA, ACA45 (FIG. 42). The gapmers were tested for their effects on ACA45 mRNA in vitro.

Hela cells were cultured on 6-well plates in DMEM medium supplemented with 10% fetal calf serum and 1% penicillin/streptomycin at 37° C. in a 5% $CO_2$ incubator.

Sub-confluent cells were treated with the antisense oligonucleotides at a 50 nM concentration in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells and ACA45 scaRNA levels were determined by northern hybridization.

Figure 43:
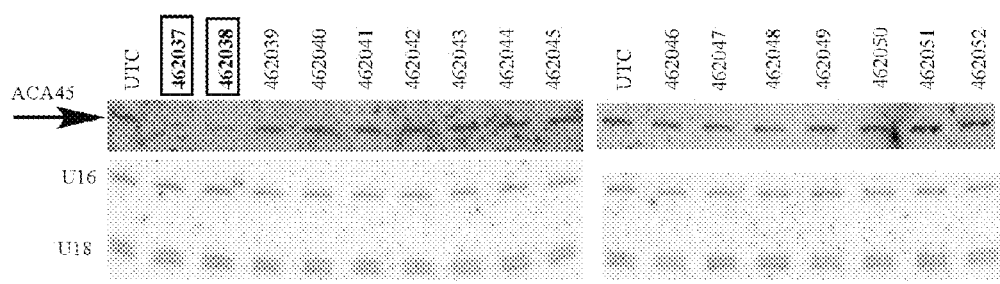
FIG. 43 shows Northern hybridization of ACA45 RNA, as described in Example 17.
Figure 44:
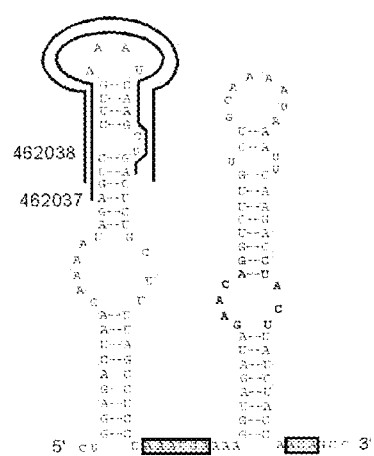
FIG. 44 shows the secondary structure of ACA45 RNA predicted using program MFold. The H and ACA motifs are boxed. The targeted positions of lead ASOs are marked by lines. The sequences predicted to guide U2 snRNA modification are shown in bold.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using an ACA45 scaRNA-specific 5'-end labeled oligonucleotide probe (5'-GCTGTTGGTAGATAAGTAGGTCT-3, designated herein as SEQ ID NO: 92). U16 and U18 snoRNAs were detected and served as a control for loading. The density of the bands was scanned using an ImageJ densitometer. Results for inhibition of U23 snoRNA are presented in FIG. 43. The data indicates that ISIS 462037 and ISIS 462038 significantly inhibited ACA45 scaRNA expression. The positions of these two antisense oligonucleotides in the secondary structure of ACA45 scaRNA are indicated by lines in FIG. 44.

The chimeric antisense oligonucleotides in Table 15 were designed as 5-10-5 MOE gapmers. The gapmers are 20 nucleotides in length, wherein the central gap segment is comprised of ten 2'-deoxynucleotides and is flanked on both sides (in the 5' and 3' directions) by wings comprising five nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. Each gapmer listed in Table 15 is targeted to SEQ ID NO: 93 (GENBANK Accession No. NR_003011.1).

TABLE 15

Chimeric antisense oligonucleotides having 5-10-5 MOE wings and deoxy gap targeted to ACA45 scaRNA

| Start Site | Stop Site | ISIS No. | Sequence | SEQ ID NO. |
|---|---|---|---|---|
| 20 | 39 | 462037 | TCAGCTTGATTTCAAGGACT | 94 |
| 21 | 40 | 462038 | GTCAGCTTGATTTCAAGGAC | 95 |
| 26 | 45 | 462039 | GCAGAGTCAGCTTGATTTCA | 96 |
| 31 | 50 | 462040 | TAAAAGCAGAGTCAGCTTGA | 97 |
| 40 | 59 | 462041 | TTAGGAGGCTAAAAGCAGAG | 98 |
| 45 | 64 | 462042 | TTCATTTAGGAGGCTAAAAG | 99 |
| 50 | 69 | 462043 | ACCTTTTCATTTAGGAGGCT | 100 |
| 57 | 76 | 462044 | TCTATCTACCTTTTCATTTA | 101 |
| 62 | 81 | 462045 | CCTGTTCTATCTACCTTTTC | 102 |
| 67 | 86 | 462046 | CAAGACCTGTTCTATCTACC | 103 |
| 72 | 91 | 462047 | GCAAACAAGACCTGTTCTAT | 104 |
| 77 | 96 | 462048 | ATTTTGCAAACAAGACCTGT | 105 |
| 92 | 111 | 462049 | GTAGGTCTTGAATTTATTTT | 106 |
| 97 | 116 | 462050 | GATAAGTAGGTCTTGAATTT | 107 |
| 102 | 121 | 462051 | TGGTAGATAAGTAGGTCTTG | 108 |
| 107 | 126 | 462052 | GCTGTTGGTAGATAAGTAGG | 109 |

Figure 45:
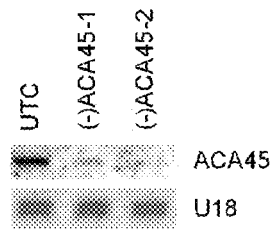
FIG. 45 shows that A H/ACA type of scaRNA can also be degraded by ASOs. Hela cells were treated for 48 hours with two different ASOs targeting ACA45 scaRNA [462037 for (−)ACA45-1 and 462038 for (−)ACA45-2]. Total RNA was prepared and subjected to northern hybridization using a 5'-end labeled probe specific to ACA45 scaRNA. U18 snoRNA was detected and served as a loading control.

In a separate experiment, Hela cells were treated for 48 hr with 50 nM of ISIS 462037 and ISIS 462038. Total RNA was prepared and subjected to northern hybridization using 5'-end labeled oligonucleotides specific to ACA45 scaRNA. U18 snoRNA (SEQ ID NO: 2) was detected and served as a loading control. The results are presented in Table 16 and FIG. 45 and demonstrate that ACA scaRNA was significantly inhibited by antisense oligonucleotides.

TABLE 16

Antisense inhibition of ACA45 scaRNA by chimeric antisense oligonucleotides

| ISIS No. | % inhibition |
|---|---|
| 462037 | 83 |
| 462038 | 87 |

Example 18: Effect of Antisense Inhibition of Human scaRNA ACA45 on its Guide Function The effect of antisense oligonucleotide-mediated ACA45 reduction on its predicted function in guiding the pseudouridylation at site U37 of U2 snRNA (Kiss A. M. et al., Mol. Cell. Biol. 24: 5797-5807, 2004) was studied.

Hela cells were cultured in DMEM medium supplemented with 10% fetal calf serum and 1% penicillin/streptomycin at 37° C. in a 5% $CO_2$ incubator. Sub-confluent cells were treated with ISIS 462038 at 50 nM concentration in Opti-MEM medium containing 4 µg/mL Lipofectamine 2000 (Invitrogen, CA) for 4 hours, after which the transfection was replaced with fresh culture medium. After a period of approximately 48 hours, RNA was isolated from the cells.

Figure 46:
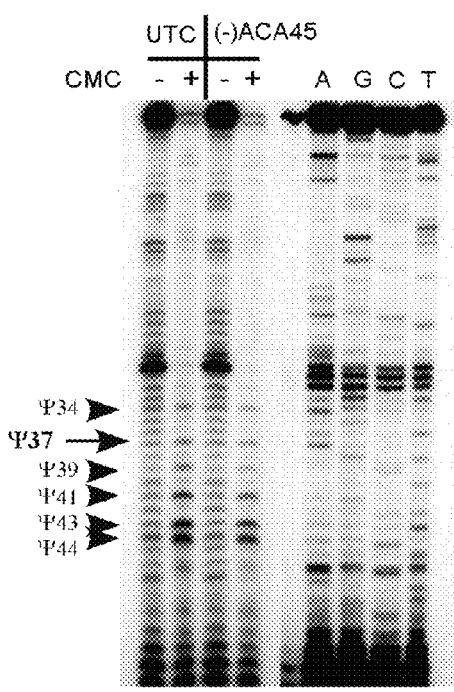
FIG. 46 shows dramatic depletion of ACA45 RNA did not disrupt pseudouridylation at the predicted site in U2 snRNA (Ψ37). Pseudouridines were detected as in panel d, using a 5'-end labeled primer specific to U2 snRNA. Extension products were separated in an 8% polyacrylamide gel, next to primer extension sequencing ladders generated using the same primer. The predicted target site (Ψ37) is indicated, and other pseudouridines detected in the same reactions are marked with arrowheads.

Total RNA from test cells was treated with N-cyclohexyl-N'-(2-morpholinoethyl)-carbodiimide methyl-p-toluolsulfonate (CMC), and subjected to primer extension analysis using a 5' end-labeled primer specific to U37 region of U2 snRNA (5'-TCGGATAGAGGACGTATCAG-3', designated herein as SEQ ID NO: 110). CMC treatment causes extension to stop one nucleotide before the pseudouridine sites. Extension products were separated in an 8% polyacrylamide gel, next to primer extension sequencing reactions preformed with the same primer. The targeted pseudouridylation site (Ψ37), as well as other pseudouridine sites, is indicated in FIG. 46.

Figure 47:
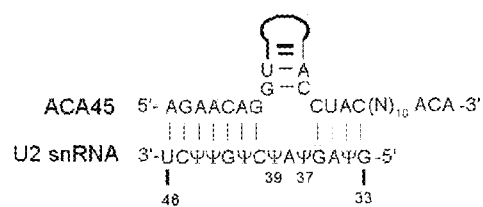
FIG. 47 shows base-pairing potential between ACA45 scaRNA and U2 snRNA. U2 snRNA sequence is numbered and the pseudouridines (Ψ) in U2 snRNA are shown.

The data in the figure demonstrates that there was no change observed for pseudouridylation at the predicted position of U2snRNA after antisense inhibition of ACA45 scaRNA. Therefore, it may be possible that ACA45 scaRNA does not have the predicted function. This theory is consistent with the observation that three nucleotides of U2snRNA are unpaired in between the two duplexes formed between U2snRNA and ACA45 RNA (FIG. 47), which is aberrant from the guide rule in which two nucleotides are unpaired (Ganot, P. et al., Cell. 89: 799-809, 1997).

Example 19: Antisense Inhibition of U16 and U50 snoRNAs in Mouse Primary Hepatocytes ISIS 462026 and ISIS 477499 were tested for their individual and combined effects on their respective targets (U16 and U50) in vitro.

Mouse primary hepatocytes were cultured on 6-well plates in DMEM medium supplemented with 10% fetal calf serum and 1% penicillin/streptomycin at 37° C. in a 5% $CO_2$ incubator. Sub-confluent cells were treated with the antisense oligonucleotides individually at a 50 nM concentration or together at 35 nM each in Opti-MEM medium containing 4 µg/mL Lipofectamine 2000 (Invitrogen, CA) for 4 hours, after which the transfection was replaced with fresh culture medium. After a period of approximately 24 hours, RNA was isolated from the cells and U16 and U50 mRNA levels were determined by northern hybridization.

Figure 48:
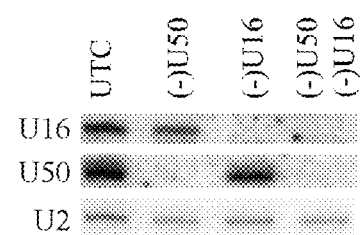
FIG. 48 shows U50 and U16 snoRNAs were depleted in mouse cells. ASO477499 and ASO462026 were transfected individually (50 nM) or together (35 nM each) into mouse primary hepatocytes using transfectamine 2000, and total RNA was prepared 24 hours after transfection. The levels of U16 and U50 were determined by northern hybridization. U2 snRNA was detected and served as a loading control. The asterisk indicates an unknown hybridization product.

Total RNA was prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using U16 snoRNA-specific 5'-end labeled oligonucleotide probe (SEQ ID NO: 2) and U50 snoRNA-specific 5'-end labeled oligonucleotide probe (SEQ ID NO: 52). U2 snRNA were detected and served as a control for loading. The density of the bands was scanned using an ImageJ densitometer. Results for inhibition of are presented in Table 17 and FIG. 48. The data indicates that ISIS 462026 and ISIS 477499 significantly inhibited their target snoRNA expressions.

TABLE 17

Antisense inhibition by chimeric antisense oligonucleotides targeted to U16 and U50 snoRNA

| ISIS | % inhibition | |
|---|---|---|
| No | U16 | U50 |
| 462026 | >95 | 0 |
| 477499 | 0 | >95 |

Example 20: In Vivo Inhibition of snoRNAs

ISIS 462026 (targeting U16) and ISIS 477499 (targeting U50), demonstrating significant inhibition of their respective snoRNAs, were tested in mice and the efficacy of the gapmers was evaluated.

Treatment

Two groups of five seven-week old balb-c mice each were administered subcutaneously with 100 mg/kg of ISIS 462026 or ISIS 477499. Another group of five mice was injected with 100 mg/kg of control oligonucleotide ISIS 141923 (CCTTCCCTGAAGGTTCCTCC, designated herein as SEQ ID NO: 111). Another group of five mice were injected subcutaneously with PBS. The mice were sacrificed 72 hours later and several tissues were harvested for target mRNA analysis. Tissues harvested were: liver, heart, spleen, white adipose tissue (WAT), kidney, and muscle.

RNA Analysis

Figure 49:
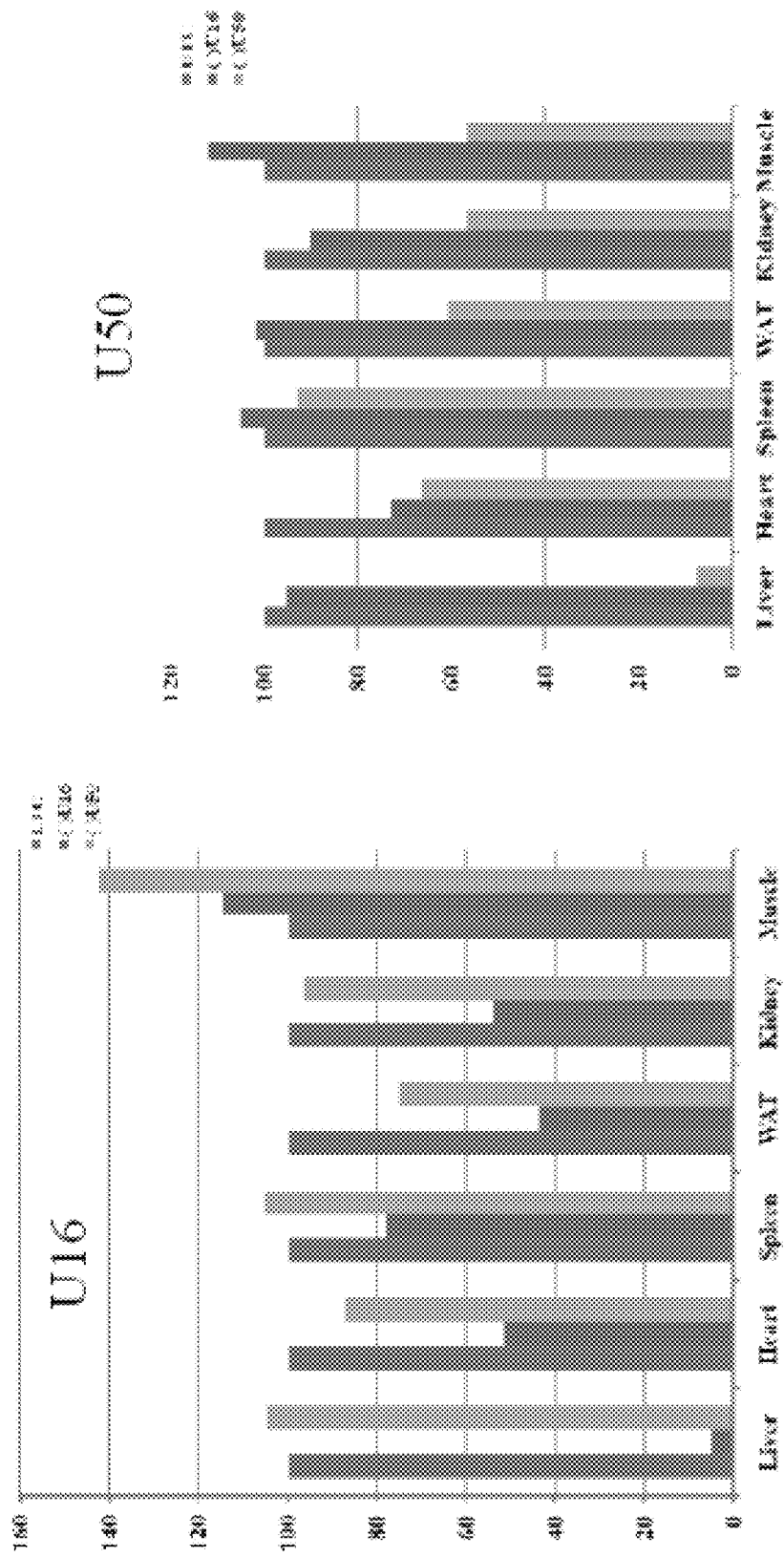
FIG. 49 shows 2'MOE/chimeric ASOs can deplete snoRNAs in mouse, as described in Example 20.

Total RNA from each of the various tissues was separately prepared using Tri-Reagent, based on the manufacturer's instructions. Five micrograms of total RNA was separated in 8% polyacrylamide-7M urea gels and was transferred onto a membrane, using semi-dry transfer apparatus. Northern hybridization was performed using U16 snoRNA-specific 5'-end labeled oligonucleotide probe (SEQ ID NO: 2) and U50 snoRNA-specific 5'-end labeled oligonucleotide probe (SEQ ID NO: 52). U2 snRNA were detected and served as a control for loading. The density of the bands was scanned using an ImageJ densitometer. Results for inhibition are presented in FIG. 49. The data indicates that ISIS 462026 and ISIS 477499 significantly inhibited their target snoRNA expressions.

Evaluation of rRNA Methylation

Total RNA was pooled for each group and subjected to primer extension analysis to detect rRNA methylation at positions A485 in 18S rRNA, targeted by U16 snoRNA, or C2613 in 28S rRNA, targeted by U50 snoRNA. The results are presented in Table 18 and FIG. 50 and demonstrate significant inhibition at 0.05 mM dNTP concentration, compared to the PBS control.

TABLE 18

Inhibition of rRNA methylation by antisense oligonucleotides in (breed) mice liver relative to the PBS control

| ISIS No | % inhibition of rRNA methylation |
|---|---|
| 462026 | >95 |
| 477499 | >93 |

Example 21: Antisense Inhibition of Nucleoplasmic Capped U1 snRNA in Mouse Primary Hepatocytes ISIS 469508 (5'-CTCCCCTGCCAGGTAAGTAT-3', designated herein as SEQ ID NO: 112), targeting U1 snRNA was tested for its effects on U1 snRNA in vitro.

Hela cells were cultured on 6-well plates in DMEM medium supplemented with 10% fetal calf serum and 1% penicillin/streptomycin at 37° C. in a 5% $CO_2$ incubator. Sub-confluent cells were treated with ISIS 469508 at a 50 nM concentration in Opti-MEM medium containing 4 µg/mL Lipofectamine 2000 (Invitrogen, CA) for 4 hours, after which the transfection was replaced with fresh culture medium. After a period of approximately 24 hours, RNA was isolated from the cells and U1 mRNA levels were determined by qRT-PCR, using primer probe sets described in FIG. 51. A forward primer T7F2 (5'-TACTTA ATAC-GACTCACTATAGGCTAGCCTCG-3', designated herein as SEQ ID NO: 113) that is specific to a mini-reporter gene derived from exons 6 to 8 of SMN2 pre-mRNA and a reverse primer SMN-E6/7R (5'-TTTTGTCTAAAAC-CCATATAATAGCC-3', designated herein as SEQ ID NO: 114) were used to detect spliced mRNA, using SMN-E6P (5'-CAGATTCTCTTGATGATGCTGATGCTTTGG-3', designated herein as SEQ ID NO: 115) as a probe. Another reverse primer SMN-I6R (5' TGTCAGGAAAAGATGCT-GAGTG 3', designated herein as SEQ ID NO: 116) was used in combination with T7F2 and SMN-E6P to detect unspliced pre-mRNA.

The results are presented in FIGS. 52 and 53. The data indicates that ISIS 469508 impaired pre-mRNA splicing. Therefore, antisense oligonucleotides can be utilized to specifically target independently transcribed nucleoplasmic snRNAs.

The invention claimed is:

1. A method of reducing the amount or activity of a target sub-nuclear RNA in a cell in an animal comprising administering to the animal a pharmaceutical composition comprising an antisense compound comprising a modified oligonucleotide complementary to the target sub-nuclear RNA; and thereby reducing the amount or activity of the target sub-nuclear RNA in the cell in the animal;
   wherein the modified oligonucleotide comprises:
   a 5'-region consisting of 1 to 7 modified nucleosides;
   a 3'-region consisting of 1 to 7 modified nucleosides; and
   a central region consisting of 5 to 28 deoxyribonucleosides; and
   wherein the animal is a mammal; and
   wherein the target sub-nuclear RNA is found in a paraspeckle, is found in a nuclear speckle, is found in a Cajal Body (scaRNA), or is a long non-coding RNA.

2. The method of claim 1, wherein at least one modified nucleoside comprises a modified sugar moiety selected from among: 2'-MOE, 2'-OMe, 2'-F, LNA, ENA, cEt, and a tetrahydropyran.

3. The method of claim 1, wherein at least one modified nucleoside comprises a modified sugar moiety selected from among: 2'-MOE, 2'-OMe, 2'-F, and a BNA.

4. The method of claim 3, wherein the BNA is selected from LNA, ENA, and cEt.

5. The method of claim 1, wherein the modified oligonucleotide comprises one or more modified internucleoside linkages.

6. The method of claim 1, wherein the antisense compound comprises a conjugate group.

7. The method of claim 1, wherein the reduced activity of the target sub-nuclear RNA results in a change in the methylation, pseudouridylation, polyadenylation, or splicing of at least one object RNA, wherein the object RNA is a RNA molecule, other than the target sub-nuclear RNA, that is affected directly or indirectly by the antisense compound.

8. The method of claim 7, wherein the reduced activity of the target sub-nuclear RNA results in a change in the methylation of at least one object RNA.

9. The method of claim 7, wherein the reduced activity of the target sub-nuclear RNA results in a change in the polyadenylation of at least one object RNA.

10. The method of claim 7, wherein at least one object RNA encodes a histone.

11. The method of claim 1, wherein the cell is a cancer cell.

12. The method of claim 11, wherein the animal has cancer.

13. The method of claim 1, wherein the animal is a human.

14. The method of claim 1, wherein the pharmaceutical composition is administered systemically.

15. The method of claim 1, wherein the pharmaceutical composition is administered by subcutaneous injection.

* * * * *

SEQUENCE LISTING

<160> NUMBER OF SEQ ID NOS: 116

<210> SEQ ID NO 1
<211> LENGTH: 150
<212> TYPE: DNA
<213> ORGANISM: Homo sapiens

<400> SEQUENCE: 1
cttcatttat atggggttat tttgcttgca atgatgtcgt aatttgcgtc ttactctgtt      60
ctcagcgaca gttgcctgct gtcagtaagc tggtacagaa ggttgacgaa aattcttact     120
gagcaagaaa taaccttgtt gtaattacta                                      150

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
ttgctcagta agaattttcg                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
attgccagtg ccgactatat                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ataaccccat ataaatgaag                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
caagcaaaat aaccccatat                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
tcattgcaag caaaataacc                                                  20

<210> SEQ ID NO 7
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 7
cgacatcatt gcaagcaaaa                                         20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
aattacgaca tcattgcaag                                         20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
acgcaaatta cgacatcatt                                         20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gtaagacgca aattacgaca                                         20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
acagagtaag acgcaaatta                                         20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
gctgagaaca gagtaagacg                                         20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
```
ctgtcgctga gaacagagta                      20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
ggcaactgtc gctgagaaca                      20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
cagcaggcaa ctgtcgctga                      20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
actgacagca ggcaactgtc                      20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
agcttactga cagcaggcaa                      20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
gtaccagctt actgacagca                      20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ccttctgtac cagcttactg                      20

<210> SEQ ID NO 20
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 20
gtcaaccttc tgtaccagct                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
ttgctcagta agaattttcg                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
atttcttgct cagtaagaat                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
aaggttattt cttgctcagt                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
acaacaaggt tatttcttgc                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
taattacaac aaggttattt                                                    20

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
gatacatcag ataggagcga a                                                  21
```

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (4)..(18)
<223> OTHER INFORMATION: bases at these positions are RNA

<400> SEQUENCE: 27
uutgcgcgcc ugcugccu                                              18

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gctactggca ggatcaacca                                            20

<210> SEQ ID NO 29
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 29
tgtttcagaa acacggacc                                             19

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 30
cagggcagaa cagatggcgt atc                                        23

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 31
accactcaga ccgcgttctc tcc                                        23

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
cagaatatca gatattttat tg                                         22

<210> SEQ ID NO 33
<211> LENGTH: 78
<212> TYPE: DNA
<213> ORGANISM: Homo sapiens

<400> SEQUENCE: 33
gatacaatga tgataacata gttcagcaga ctaacgctga tgagcaatat taagtctttc      60
gctcctatct gatgtatc                                                    78

<210> SEQ ID NO 34
<211> LENGTH: 77
<212> TYPE: DNA
<213> ORGANISM: Homo sapiens

<400> SEQUENCE: 34
cagaatacat gatgatctca atccaacttg aactctctca ctgattactt gatgacaata      60
aaatatctga tattctg                                                     77

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
tatgttatca tcattgtatc                                                  20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gctgaactat gttatcatca                                                  20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
ttagtctgct gaactatgtt                                                  20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
atcagcgtta gtctgctgaa                                                  20

<210> SEQ ID NO 39
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 39
attgctcatc agcgttagtc                                            20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
acttaatatt gctcatcagc                                            20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gataggagcg aaagacttaa                                            20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
atacatcaga taggagcgaa                                            20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
tgagatcatc atgtattctg                                            20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
gttggattga gatcatcatg                                            20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
agttcaagtt ggattgagat                                            20

```
<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
gtgagagagt tcaagttgga                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gtaatcagtg agagagttca                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
tcatcaagta atcagtgaga                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
tttattgtca tcaagtaatc                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
cagatatttt attgtcatca                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
cagaatatca gatattttat                                              20

<210> SEQ ID NO 52
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 52

```
ggttcgggat aagatcatca ca                                              22
```

<210> SEQ ID NO 53
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 53

```
cgtacttatt tttcttcagg tta                                             23
```

<210> SEQ ID NO 54
<211> LENGTH: 5001
<212> TYPE: DNA
<213> ORGANISM: Homo sapiens

<400> SEQUENCE: 54

```
gacggacaaa caagttgcag aacatataga tcccatttgt atgtgaaaaa cgaagtacat     60
atatttgcat ttgcatagga agtctcaaaa actgttaaca gtggtattgc tgaagagtac    120
aactagggag aagattccca ggcatgtgga agatacttt cactttgctt tttttgttaa    180
ctcttttaa aaattttttt aatacaatag agacagggtc ttgggctcaa tcctcccacc    240
tcagcctcca aaagtgctct aattacagac ataagccacc acaccgggcc tactttgctt   300
cttatatcct tttgtactgt attgtttgtt ttactattta ctatgagcaa tatgcaaatt    360
tatgtaagac attacaaagt aatacaaaaa ccgacaaaat gcccggccca gtcaatactt    420
catcatatag gttcctgtta gagaaaagtg cttttcacta ctatctttga atgtgaagtt    480
tgatcttcat tctaattttc taaaaagcca ccgaatgtat tgttcattc attcattcat    540
ttaaccatta ccgacaacct acttaatgct aggcactgtt ctaagaaaaa ataaacagca    600
gagcacgaaa tcagatgtgt tgctcccaca ctctagcaga atcggaccgt aatcaaatgc    660
acacataaac aactttaata agtagtgctt tgaaatatag aagtgaagaa cgacctgaat    720
tttcaaatac tgaaatgttc aaatgtcgtg tgcacacaca cacacgcaga catattcact    780
cgaacatgct aattaatcaa agcactgctt ttgaattttg tgtttgtcgt ctggataaag    840
tattcaggga tacttctcaa attaatcttt ctctcgtttt caatataact aattgagtac    900
aaagaagtta aaaattagca aagcatttca gctgtgtgac cttaggcaaa ttacctggct    960
gttttaagcc tcagttttct cctctgcgaa atggagtatt gaacctcacg ttcgctgttt   1020
gagggagact tgtatggtca cgtttagtgt aaccggatgc ctggcacgag gaagcgtgag   1080
gaggaatgga tccccatggg gccttgatgc ccgccctgag gccctgcagg gccgcacgcc   1140
ggggctgttc tcacgtggcg cttttccgctt tttcacccaa gcgtttctgc cagccaactg   1200
cccttttccg gagtgctgcg gccagggctc gcccgctcct ccggcggcct ccgctggggg   1260
cccactacag cccagcgcca gccagccagc cagcccagct tctcgaatcg gtcctaagct   1320
gaggccgccc tgcgctgcaa aacttgtgtc cactctcgga cccaatctgt cctggacgga   1380
cttggctcgt ggcaggcgaa agcgtcgttt ccaactgcag ctgtttgaat tctgcgcca   1440
cacccgcgcc acgtagggcc aagtcggccg ccagactcgt aagagacgct tcgcagtgcg   1500
cctgcgggcg cgcgccggga aatggccggg cgcgcggccg gcctgcgcg cgctccacaa    1560
cgcggaacgg gcctcagaag agccaccgcg cgcgctcccg ctaattcgcg accacacccc   1620
tgtctacttc catgtccaat aggtgcgaga gggcgggacg gcctcgttct gactccggga   1680
```

```
ggctatataa ggagctactg gctgcgcact tcggtctttt acgtcggcct tcgcgagcgt   1740
ctgggcgggt ggtaggtgag tgggtattgc gggctagtat ccgagcaaaa gatggtggcg   1800
caggccgagt taagagcttt aatcctgtga agacatctta gtgaagagtt tagagtgctg   1860
agagttgaaa gcttgcacgt gggaaacgtg cggccggact gccacatgta ctgaggttga   1920
gtcgtgacgg ccacaggctc cgagttttgg cgtgaggaac cgctgatcgg ccacgggcgc   1980
cgaacttgct ggcctccggc atgtgcctga gcggcggcgg aaaaaccacc ttaattgggg   2040
cggagggtta gttttaacag caaagggcct ttactaaaat ggcgaaggcc ttccgtcggc   2100
gttgttttaa aatgggaagc ctcgaccctg tattgaaact gagctgttcg aaggcggcgt   2160
tgtgtgcaat tcggattaat gaaggggaag ggttttgtgt ggaaaaacgc cttggagtgt   2220
gacatttctg cgagaatgct aaataccga tttcccgcag gaacaatggc gctgtcttca   2280
gtggcacagt ggagcagctc tgaagatgca aaggtaagag cttagttaag cttagtttcc   2340
aaactaaagg agtaaacctg ttgatttaca ggaataggaa ctgttgcatc gtttgaaatt   2400 tactttttt tgttagatac acgaaaaaac ttccagaaca tctgggagaa tatttaatgg   2460
aaaatcgctt ggttaaaacc tgacactttt aacaggtatg tgttgttta gtactttatg   2520 attgagcata gcatttaatc cacacctaga ctaaatcaaa ttttttttgt cagtgaacag   2580
cgttctgagt gtggacgagt agccagtgaa gataatgaat gtcgaatgtg actgactagc   2640
agcttcattt tgaagtaggt tgtatggctt aaaagttctg tagtatttgt actataatac   2700 ttgccttta gcattacctt ggtttgtagt cagtgtcaca gaagtgcagt ttaatgtatt   2760
atgtgtacat atacaaggtc tgattggtct aatcaatgat gaaacctatc ccgaagctga   2820
taacctgaag aaaaataagt acggattcgg cttctgagat taagaccagt aattcagagg   2880
tggagtaaat tttgttgccg tgatttata acagttgtgt tataaaatcc tgggttttt   2940 tttttctgc caacagtgag ggtcgctgtc tgcccattga tagaggccag attgtcttgg   3000
aagttccaaa gttgcaacga tttctgtaag tggagttttt ctgtttgctt agagatcagt   3060
gaatattgtg tccttggtct tatctgtgat gatcttatcc cgaacctgaa cttctgttga   3120
aaaaaaaaaa cttttacgga tctggcttct gagatggacc gttataagga caatatttt   3180 ttttaatact tttaatgctt ttacatatgt tgtaatgttt gtagtcttgt aagaatctcg   3240 tgttttcct tttctagggc tagtgccacg aggtttactt gactgttgtg tgaaaagctg   3300
ataagaaaac catccagaaa aaagctcttc gttttacaaa catgaaaata aacatgtaa   3360 ttttggatta tgttccttt tgttattact tttaaatagg tcctgaaata acatggggag   3420
cattaaatgg aaaatccact aaccagcctt gtaatcaaat tactgtgagt gaatgtttcg   3480
ggtttgtgca gggtacaatg taaggtttt tggatcagtg taagagtgga gagacaggaa   3540
ttagaagtaa ttgttactaa gcaaatcatg gaatatttag ttttgatgta actataattt   3600
tgaaagcctg gatgcttaag ttgagaaatg ggggaatgag atacagaaaa taaggagcac   3660
aatagaataa taatagcagt ttattaagta tggtcatgag ggaaggttac tgataaaaca   3720
atctggtaaa gacattcagg cttgctaaaa tctaggaaga ggtcatttgg caggatgggt   3780
tacataatgc tatctgatac taccaaataa aatgagagag aagccttagg catgtaacgt   3840
ttggagatag aaaatgtacc ttcactatga aggtagtgtg tgtaagatgg cagttgaaag   3900
cattgcttgt gtttatgttt ataccttga tctctgatgc ccttacctac cgtacttaaa   3960
actctgttaa tcattgtctt tctccccctc ccacaacttc tgcataaaat tttaagatct   4020
```

```
gtgtttcatt agttcaagag tgcctagaat agggccaggc actgttatac agtatgtggt    4080
aaaagactat tgagattcca gttttcaagg aagagtgcca ttaccgtttt gttaaagctg    4140
gcaaacaaga caaagttgtg aaatagactg gttgctttgg agccctctga ccgcttttcc    4200
tgtagctcct tctacctccc ttgcctccca atagattttt taatatgtca cattatctat    4260
cgaaattagt actccacatt tatatgcact ggcttgtgct aggctctgcc aagactcctg    4320
aaataaaacc gttttgtcaa cagtggcaca agatgccaag gaaaagtcaa gctatgaagg    4380
attcttgaaa atagaacaag tggatttgag tctaaaccag cacagatgtt gggacaatag    4440
gcctaagaaa taactgagca agacagtat ggttcagagt ctgagacaaa tattgaggat    4500
ttgggtacca acagggtgga taggtgtagg acagaaaact gatgttataa atacccttaa    4560
gattcttgag caaggaagtt acaaatgtaa gactattcct gtaatgagag tcagatccaa    4620
aaaggtttaa tttgaatgga attgaacttg aaagttcagt ttcaattact gactccttga    4680
tggcaatttc taatcacaca ggaggctgtt agtctgtcat agcctcctaa aatctcaggc    4740
gatattggtt aagatcagtt tcctaagttt accctccaga gcatagctgc tgcttgggac    4800
caggtgcagt gactcatgcc tgtaatccca gcactctgct tgagcccagg aagagaccag    4860
cctggaaaca gcaagttgtc atctctataa ataagtaaaa ctgggtgtgg taacatgcgc    4920
ttgttccagc tactcgggag gctgagatag gaggatcact tgaacctagg aggttgaagc    4980
tacaatcagc catgattgca c                                              5001
```

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55

```
ggataagatc atcacagata                                                  20
```

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56

```
gttcgggata agatcatcac                                                  20
```

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57

```
ttcaggttcg ggataagatc                                                  20
```

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
agaagttcag gttcgggata                                                   20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
tcaacagaag ttcaggttcg                                                   20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
aagccagatc cgtaaaagtt                                                   20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ctcagaagcc agatccgtaa                                                   20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
ctcagaagcc gaatccgtag                                                   20

<210> SEQ ID NO 63
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 63
tggaacgctt cacgaatttg cg                                                22

<210> SEQ ID NO 64
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 64
gaatgtctca caatacagct aaat                                              24

<210> SEQ ID NO 65
<211> LENGTH: 21
<212> TYPE: DNA

```
<213> ORGANISM: Artificial Sequence
<220> FEATURE:
<223> OTHER INFORMATION: Synthetic oligonucleotide

<400> SEQUENCE: 65
ctggatcaga acttgactat c                                            21

<210> SEQ ID NO 66
<211> LENGTH: 137
<212> TYPE: DNA
<213> ORGANISM: Homo sapiens

<400> SEQUENCE: 66
gtcttctcat tgagctcctt tctgtctatc agtggcagtt tatggattcg cacgagaaga    60
agagagaatt cacagaacta gcattatttt accttctgtc tttacagagg tatatttagc   120
tgtattgtga gacattc                                                  137

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
aaggagctca atgagaagac                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
acagaaagga gctcaatgag                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
gatagacaga aaggagctca                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
ccactgatag acagaaagga                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
```
aactgccact gatagacaga                                          20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
ccataaactg ccactgatag                                          20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
cgaatccata aactgccact                                          20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
tcgtgcgaat ccataaactg                                          20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
tcttctcgtg cgaatccata                                          20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
tctcttcttc tcgtgcgaat                                          20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
aattctctct tcttctcgtg                                          20

<210> SEQ ID NO 78
<211> LENGTH: 20
<212> TYPE: DNA

<213> ORGANISM: Artificial Sequence
<220> FEATURE:
<223> OTHER INFORMATION: Synthetic oligonucleotide

<400> SEQUENCE: 78
ctgtgaattc tctcttcttc					20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
tagttctgtg aattctctct					20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
aaaataatgc tagttctgtg					20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
aaggtaaaat aatgctagtt					20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
gacagaaggt aaaataatgc					20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
gtaaagacag aaggtaaaat					20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
cctctgtaaa gacagaaggt					20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
atatacctct gtaaagacag                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
gctaaatata cctctgtaaa                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
atacagctaa atatacctct                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
tcacaataca gctaaatata                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
atgtctcaca atacagctaa                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
gaatgtctca caatacagct                                               20

<210> SEQ ID NO 91
<211> LENGTH: 22
<212> TYPE: DNA
<213> ORGANISM: Artificial Sequence
<220> FEATURE:

<223> OTHER INFORMATION: Synthetic oligonucleotide

<400> SEQUENCE: 91
aaggaaccat aactgattta at						22

<210> SEQ ID NO 92
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 92
gctgttggta gataagtagg tct					23

<210> SEQ ID NO 93
<211> LENGTH: 127
<212> TYPE: DNA
<213> ORGANISM: Homo sapiens

<400> SEQUENCE: 93
ctggagacta agaaaataga gtccttgaaa tcaagctgac tctgctttta gcctcctaaa		60 tgaaaaggta gatagaacag gtcttgtttg caaaataaat tcaagaccta cttatctacc		120 aacagca									127

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
tcagcttgat ttcaaggact						20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
gtcagcttga tttcaaggac						20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
gcagagtcag cttgatttca						20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
taaaagcaga gtcagcttga						20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
ttaggaggct aaaagcagag                                          20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
ttcatttagg aggctaaaag                                          20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
accttttcat ttaggaggct                                          20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
tctatctacc ttttcattta                                          20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
cctgttctat ctaccttttc                                          20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
caagacctgt tctatctacc                                          20

<210> SEQ ID NO 104
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 104
gcaaacaaga cctgttctat                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
attttgcaaa caagacctgt                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
gtaggtcttg aatttatttt                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
gataagtagg tcttgaattt                                               20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
tggtagataa gtaggtcttg                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
gctgttggta gataagtagg                                               20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
tcggatagag gacgtatcag                                               20

```
<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
ccttccctga aggttcctcc                                                    20

<210> SEQ ID NO 112
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 112
ctcccctgcc aggtaagtat                                                    20

<210> SEQ ID NO 113
<211> LENGTH: 26
<212> TYPE: DNA
<213> ORGANISM: Artificial Sequence
<220> FEATURE:
<223> OTHER INFORMATION: Primer

<400> SEQUENCE: 113
atacgactca ctataggcta gcctcg                                             26

<210> SEQ ID NO 114
<211> LENGTH: 26
<212> TYPE: DNA
<213> ORGANISM: Artificial Sequence
<220> FEATURE:
<223> OTHER INFORMATION: Primer

<400> SEQUENCE: 114
ttttgtctaa aacccatata atagcc                                             26

<210> SEQ ID NO 115
<211> LENGTH: 30
<212> TYPE: DNA
<213> ORGANISM: Artificial Sequence
<220> FEATURE:
<223> OTHER INFORMATION: Probe

<400> SEQUENCE: 115
cagattctct tgatgatgct gatgctttgg                                         30

<210> SEQ ID NO 116
<211> LENGTH: 22
<212> TYPE: DNA
<213> ORGANISM: Artificial Sequence
<220> FEATURE:
<223> OTHER INFORMATION: Primer

<400> SEQUENCE: 116
tgtcaggaaa agatgctgag tg                                                 22
```